(12) United States Patent
Maheshwari et al.

(10) Patent No.: US 10,561,748 B2
(45) Date of Patent: Feb. 18, 2020

(54) ANTHRANILIC ACID DERIVATIVES

(71) Applicant: Divya Maheshwari, Mumbai, Maharashtra (IN)

(72) Inventors: Divya Maheshwari, Maharashtra (IN); Uday Balkrishna Gokhale, Maharashtra (IN)

( * ) Notice: Subject to any disclaimer, the term of this patent is extended or adjusted under 35 U.S.C. 154(b) by 161 days.

(21) Appl. No.: 15/510,293

(22) PCT Filed: Sep. 21, 2015

(86) PCT No.: PCT/IB2015/057254
§ 371 (c)(1),
(2) Date: Mar. 10, 2017

(87) PCT Pub. No.: WO2016/051306
PCT Pub. Date: Apr. 7, 2016

(65) Prior Publication Data
US 2017/0281805 A1  Oct. 5, 2017

(30) Foreign Application Priority Data
Oct. 3, 2014 (IN) .................. 3148/MUM/2014
Nov. 13, 2014 (IN) .................. 3588/MUM/2014

(51) Int. Cl.
*A61K 51/00* (2006.01)
*A61M 36/14* (2006.01)
*A61K 51/04* (2006.01)
*C07D 401/12* (2006.01)

(52) U.S. Cl.
CPC ........ *A61K 51/0455* (2013.01); *C07D 401/12* (2013.01); *C07B 2200/05* (2013.01)

(58) Field of Classification Search
CPC .............. A61K 51/0455; C07D 401/12; C07B 2200/05
USPC ...................................................... 424/1.89
See application file for complete search history.

(56) References Cited

U.S. PATENT DOCUMENTS 6,218,393 B1    4/2001  Ryder et al.
2004/0087568 A1  2/2004  Huang et al.

OTHER PUBLICATIONS

Kawamura et al. Bioorg. Med. Chem. 19 (2011) 861-870.*
Zhang et al. Curr. Top. Med. Chem. 2007, 7, 1817-1828.*
Donohue et al. J. Med. Chem. 2008, 51, 5833-5842.*
Hendrikse et al. Cancer Res. 1999, 59, 2411-2416.*
PCT International Search Report issued in PCT/IB2015/057254 dated Sep. 2, 2016.
Written Opinion of the International Searching Authority issued in PCT/IB2015/057254 dated Sep. 2, 2016.
Pubchem, Substance Record for SID 124958506 Create Date: Aug. 19, 2011. [retrieved on May 17, 2016]. Retrieved from the Internet: <https://pubchem.ncbi.nlm.nih.gov/substance/124958506>. entire document.

* cited by examiner

*Primary Examiner* — Michael G. Hartley
*Assistant Examiner* — Sean R Donohue

(57) ABSTRACT

The present invention is directed to a novel compound of Formula 1 wherein the radiolabeled compound of Formula 1 is capable of being used as a radiotracer in PET imaging of a targeted localized tissue and targeted radionuclide therapy of one or more conditions that may be regulated or normalized via inhibition of transporter such as Pgp, BCRP or MRP I. The novel compounds of Formula 1 can also be used as substrates for binding with one or more ABC transporters. In particular, the present invention aids in diagnosis and therapeutic treatment of MDR disorders in all forms of cancers and neurological disorders of the central nervous system. The present invention further provides methods of preparation of compounds of Formula 1 and novel intermediates used in the preparation of compounds of Formula 1.

5 Claims, 5 Drawing Sheets

ANTHRANILIC ACID DERIVATIVES

CROSS REFERENCE TO RELATED APPLICATIONS

The present application is a § 371 National Phase application based on PCT/IB2015/057254 filed Sep. 21, 2015, which claims the benefit of Application Nos. 3148/MUM/2014, filed Oct. 3, 2014 and 3588/MUM/2014, filed Nov. 13, 2014, the subject matter of each of which is incorporated by reference in their entirety.

FIELD OF THE INVENTION

The present invention relates to novel Anthranilic acid derivatives of Formula 1, and their uses as ABC (ATP-binding cassette) transporter substrates and radiotracers for PET imaging and targeted radionuclide therapy of one or more conditions that may be regulated or normalized via inhibition of ABC transporter. The present invention further provides methods of preparation of the compounds of Formula 1 and intermediates of Formula 2 in preparation of the compounds of Formula 1.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

ATP-binding cassette transporters (ABC transporters) are members of a protein superfamily that is one of the largest and oldest families with representatives in all extant phyla from prokaryotes to humans. ABC transporters are transmembrane proteins that utilize the energy of adenosine triphosphate (ATP) binding and hydrolysis to carry out certain biological processes including translocation of various substrates across membranes and non-transport-related processes such as translation of RNA and DNA repair. They transport a wide variety of substrates across extra- and intracellular membranes, including metabolic products, lipids and sterols, and drugs. Proteins are classified as ABC transporters based on the sequence and organization of their ATP-binding cassette (ABC) domain(s). ABC transporters are involved in tumor resistance, cystic fibrosis and a range of other inherited human diseases along with both prokaryotic and eukaryotic (including human) development of resistance to multiple drugs.

ABC transporters utilize the energy of ATP binding and hydrolysis to transport various substrates across cellular membranes. They broadly function in different ways—firstly as importers, they mediate the uptake of nutrients into the cells, secondly as exporters or effluxers, when they function as pumps that extrude toxins and drugs out of the cell and lastly do not function as transporters, but are rather involved in translation and DNA repair processes. P-glycoprotein (P-gp) is one of the important proteins of the ABC (ATP—binding cassette) superfamily. This protein can export an astonishing variety of amphipathic drugs, natural products, and peptides from mammalian cells, powered by the energy of ATP hydrolysis.

Noninvasive, nuclear imaging techniques can be used to obtain basic and diagnostic information about the physiology and biochemistry of living subjects, including experimental animals, normal humans and patients. These techniques rely on the use of imaging instruments that can detect radiation emitted from radiotracers administered to living subjects. The information obtained can be reconstructed to provide planar and tomographic images which reveal the distribution and/or concentration of the radiotracer as a function of time.

Diagnostic techniques in nuclear medicine use radioactive tracers which emit gamma rays from within the body. These tracers are generally short-lived isotopes linked to chemical compounds which facilitate investigations of specific physiological processes. They can be given by injection, inhalation or orally. The first types are where single photons are detected by a gamma camera which can view organs from many different angles. The camera builds up an image from the points from which radiation is emitted; this image is enhanced by a computer and viewed by a physician on a monitor for indications of abnormal conditions. A more recent development is Positron Emission Tomography (PET) which is a more precise and sophisticated technique using isotopes produced in a cyclotron. A positron-emitting radionuclide is introduced, usually by injection, and accumulates in the target tissue. As it decays it emits a positron, which promptly combines with a nearby electron resulting in the simultaneous emission of two identifiable gamma rays in opposite directions. These are detected by a PET camera and give very precise indication of their origin. PET's most important clinical role is in oncology, diseases of the central nervous system, etc. The most commonly used positron-emitting radionuclides are $^{15}$O, $^{13}$N, $^{11}$C and $^{18}$F, which are usually accelerator-produced and have a half life of 2, 10, 20 and 110 minutes, respectively. The most widely used gamma-emitting radionuclides are $^{18}$F, $^{99}$mTc, $^{201}$Tl and $^{123}$I.

Numerous formulations and compounds with fluorine-18 as the radio isotope are known in the prior art, since it has proven to be the most accurate non-invasive method of detecting and evaluating most cancers. Gamma imaging provides a view of the position and concentration of the radioisotope within the body. Organ malfunction can be indicated if the isotope is either partially taken up in the organ (cold spot), or taken up in excess (hot spot). If a series of images is taken over a period of time, an unusual pattern or rate of isotope movement could indicate malfunction in the organ.

While there has been vast improvement in diagnostics techniques, it has also been observed that many/certain drugs tend to become ineffective and lose their efficacy after certain time. This has been variously attributed to multi drug resistance (MDR). It affects patients with various ailments including a variety of blood cancers and solid tumors, such as breast, ovarian, lung, and gastrointestinal tract cancers. Drug resistance associated with drug efflux, mediated by ATP transporters such as Pgp, BCRP and MRP1 is reported in mammalian cells.

Pgp, BCRP and MRP1 are important ATP Binding Cassette transporter widely expressed in the body and play a crucial role in Multidrug Resistance (MDR). P-glycoprotein is the best-studied efflux pump and as such has offered important insights into the mechanism of bacterial pumps. For these reasons P-gp represent a new potential marker useful in monitoring and diagnosis of resistant tumors. In the last decade several efforts have been addressed in searching compounds able to interact with the pump with different mechanism. These compounds could be radiolabeled with $^{11}$C and $^{18}$F and employed as P-gp tracer by PET techniques. Failure of chemotherapy due to MDR1/P-gp mediated resistance is a well-characterized biomarker of a more aggressive and malignant phenotype in breast cancer pathology. Currently there are no methods or tests available to assess or detect the cause of multi drug resistance in patients.

U.S. Pat. No. 7,989,630 discloses a method of using a substrate for P-glycoprotein where the substrate carries $^{18}F(CH2)2$ {$[^{18}F]F$ fluoroethyl} as a Positron Emission Tomography (PET) radio tracer for detecting cancer such as breast cancer.

Kazunori Kawamura, et al. "Synthesis and in vivo evaluation of 18F-fluoroethyl F120918 and XR9576 as positron emission tomography probes for assessing the function of drug efflux transporters" *Bioorganic & Medicinal Chemistry*, 19(2), pp 861-870 (2011) alludes to the possibility of the $[^{18}F]$-Tariquidar being a substrate for drug efflux transporters. Tariquidar is Pgp inhibiter currently under clinical trials which non-competitively binds to the p-glycoprotein transporter, thereby inhibiting transmembrane efflux of anticancer drugs.

Thomas Wanek, et al. , "A comparative small-animal PET evaluation of [11C]tariquidar, [11C]elacridar and (R)-[$^{11}C$] verapamil for detection of P-glycoprotein-expressing murine breast cancer" *European Journal of Nuclear Medicine and Molecular Imaging*, 39(1), pp 149-159 (2012) discloses a method of using radio-labeled [$^{11}C$]tariquidar in Positron Emission Tomography (PET) evaluation for detecting P-glycoprotein-expressing murine breast cancer.

A number of PET and SPECT (single photon emission tomography) tracers have been developed to demonstrate the presence of P-gp in tissue, but none of these tracers are applied to drug development or currently used as routine clinical diagnostic tool. Although these imaging tools have their utility, their sensitivity and therefore their scope for research purposes is limited. At most, a 2-3 fold increase of uptake in the P-gp expressing tissue (brain/tumour) is observed at the assumed 100% inhibition dose. This means that if small changes (e.g. <20%) in P-gp functionality suffice for co-treatment in for example tumour therapy, current imaging tools may not be sensitive enough to establish the change in P-gp functionality with sufficient confidence and may therefore not be suitable for establishing the required dose of P-gp inhibitor or competitive substrate. The P-gp transport system is complex and poorly understood in man in vivo and highly sensitive radiotracers which could be used in vivo would be especially beneficial in elucidating P-gp's role in drug and toxin resistance, immunity, apoptosis or cell differentiation.

Several ligands have been developed and radiolabeled to image P-gp (vepamil, tariquidar, elacridar, N-desmethyloperamide) and today [$^{11}C$]verapamil is the only one used in clinical studies. Tariquidar is a P-gp inhibitor currently under clinical trials.

The radiotracers have been limited in clinical application because of different in vivo behavior, with respect to preliminary in vitro studies, by low uptake and selectivity and presence of radio metabolites.

There is thus a need in the art to develop novel anthralinic acid derivatives which are capable of being used as radiotracers in PET imaging, as well as targeted radionuclide therapy of one or more conditions that may be regulated or normalized via inhibition of ATP transporters selected from P-gp, BCRP and MRP1. Further, it would be more beneficial if such new compounds can also be used as substrates for these ABC transporters to study in-vitro and in-vivo over-expression of ATP transporters and diagnosis of MDR.

The present invention satisfies the above needs and overcomes the deficiencies generally found in the prior art.

OBJECTS OF THE INVENTION

It is an object of the present invention to provide a novel compound of Formula 1 capable of being used as a substrate for at least one ABC transporter selected from Pgp, MRP1 or BCRP.

It is another object of the present invention to provide a novel compound of Formula 1 capable of being used as a radiotracer for PET imaging and targeted radionuclide therapy of one or more conditions that may be regulated or normalized via inhibition of ABC transporters such as Pgp, MRP1 or BCRP.

It is a further object of the present invention to provide a novel compound of Formula 1 which can be used as radiotracer for target detection and quantitative imaging of Pgp and provide a non-invasive means/ tool to detect MDR pathology and assign MDR 1/Pgp as the cause of drug resistance in patients exhibiting disease progression or impairment due to failure of chemotherapy.

It is an object of the present invention to provide a novel compound of Formula 1 which can be used as radiotracers for target detection and quantitative imaging of P-glycoprotein and provide a non-invasive means/ tool to detect MDR pathology and assign MDR 1/Pgp as the cause of drug resistance in cancer patients exhibiting disease progression or impairment due to failure of chemotherapy to enable for patients stratification based on therapeutic response and guidance to design a bio-marker specific treatment regime and ensure unnecessary toxicities and improve survival outcomes and overall quality of life for the patient.

It is an object of the present invention to provide a novel compound of Formula 1 which has good affinity to bind at least one ABC transporter selected from Pgp, MRP1 or BCRP.

SUMMARY OF THE INVENTION

The present invention provides a novel compound of Formula 1 or its pharmaceutical acceptable salts thereof.

The present invention further provides a novel compound of Formula 1 capable of being used as a substrate for at least one ABC transporter selected from Pgp, MRP1 or BCRP.

In one aspect, the present invention provides a novel compound of Formula 1 capable of being used as a radiotracer for PET imaging and targeted radionuclide therapy of one or more conditions that may be regulated or normalized via inhibition of ABC transporter.

The present invention also provides diagnostic compositions comprising a compound of Formula 1 and pharmaceutically acceptable carrier or diluent.

The present invention further provides a method of detecting/ imaging a site of targeted localized tissue, the method comprising introducing into a subject a detectable quantity of a radiolabeled compound of Formula 1. The targeted localized tissue, for example, can be tumour or any growth/ proliferation.

The present invention further provides a method for inhibiting ATP transporter function, the method comprising administering to a mammal an ATP transporter inhibiting amount of a compound of Formula 1 or a pharmaceutically acceptable salt thereof.

In one aspect of the present invention, the ABC transporter is preferably selected from Pgp, BCRP or MRP1.

In some embodiments, the present invention provides a method for detecting MDR 1/Pgp mediated resistance, the method comprising introducing into a subject harbouring a tumour/malignant growth a detectable quantity of a radio-labeled compound of Formula 1, or its pharmaceutically acceptable salts thereof.

In some embodiment of the present invention, compound of Formula 1 or its pharmaceutically acceptable salts thereof can be radio labelled with positron-emitting radionuclides such as $^{15}O$, $^{13}N$, $^{11}C$, $^{18}F$, $^{68}Ga$, $^{89}Zr$ and $^{94}Tc$ and gamma-emitting radionuclides are $^{18}F$, $^{99m}Tc$, $^{201}Tl$ and $^{123}I$. A further aspect of this invention is directed to methods of preparation of a compound of Formula 1. The present invention also provides a novel intermediate of Formula 2 useful in preparation of a compound of Formula 1.

A further aspect of this invention is directed to methods of preparation of a compound of Formula 1. The present invention also provides a novel intermediate of Formula 2 useful in preparation of a compound of Formula 1.

BRIEF DESCRIPTION OF THE DRAWINGS

The embodiments herein will be better understood from the following detailed description with reference to the drawings, in which:

FIG. 1 illustrates an HPLC chromatogram of Compound of Formula 1a

DETAILED DESCRIPTION OF THE INVENTION

Figure 1:
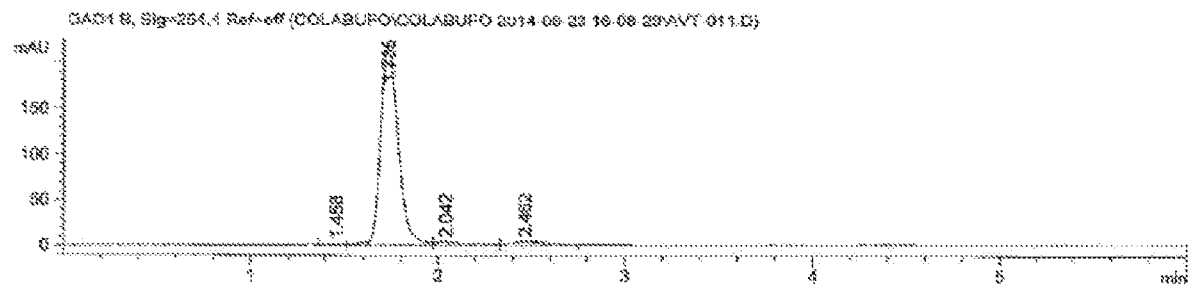

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The headings and abstract of the invention provided herein are for convenience only and do not interpret the scope or meaning of the embodiments.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The present invention is directed to a novel compound of Formula 1,

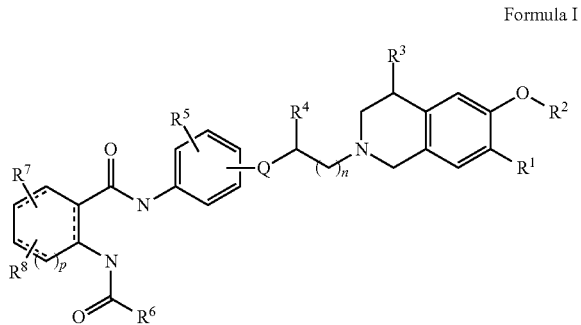

Formula I or a pharmaceutically acceptable salt thereof; wherein,
$R^1$ is methoxy;
$R^2$ is $—(CH_2)_m X$ wherein X is halogen or an radioactive isotope;
$R^3$ is selected from H or $—C_1$-$C_6$ alkyl;
$R^4$ is selected from H, $—O—C_1$-$C_6$ alkyl or $—C_1$-$C_6$ alkyl;
$R^5$ is selected from H, $—C_1$-$C_6$ alkyl or $—C_1$-$C_6$ alkoxy;
Q is selected from a group consisting of a direct bond, O, S, $—S—(CH_2)_m—$ or $—O—(CH_2)_m—$
wherein m is an integer selected from 1, 2, 3, 4, 5 or 6;
"═══" is either a single bond or double bond;
$R^6$ is selected from the group consisting of aryl, 5-10 membered heteroaryl and 3-14 membered heterocyclyl ring;
$R^7$ and $R^8$ are same or different and are independently selected from the group consisting of H, $C_1$-$C_6$ alkyl, $C_1$-$C_6$ alkoxy, hydroxy, halogen, phenyl, —NHOH, nitro, a group $N(R^{10}R^{11})$ as defined above or a group $SR^{11}$ wherein $R^{10}$ and $R^{11}$ can independently be H or $C_1$-$C_6$ alkyl; or $R^7$ and $R^8$, when attached on adjacent carbon atoms, join together with the carbon atoms to which they are attached, to form a benzene ring or a methylenedioxy substituent;
n is 0 or an integer selected from 1, 2, 3, 4, 5 or 6; and
p is 0 or an integer selected from 1, 2 or 3.

The term "alkyl" as used herein alone or as part of another group refers to a straight or branched chain aliphatic hydrocarbon chain, having from 1 to 6 carbon atoms. Examples of alkyl include, but are not limited to methyl, ethyl, n-propyl, isopropyl, n-butyl, n-pentyl, i-butyl and the like. Alkyl groups may optionally be substituted with one or more substituents selected from halogen, —OH, $C_1$-$C_6$ alkoxy or haloalkyl.

The term "alkoxy" as used herein alone or as part of another group refers to O-alkyl wherein alkyl is the same as defined above. Alkoxy groups may optionally be substituted with one or more substituents selected from halogen, —OH, $C_1$-$C_6$ alkyl or haloalkyl.

The term "aryl" as used herein refers to six to ten membered monocyclic aromatic group, for example phenyl or naphthyl ring and the like optionally substituted with one or more substituents selected from H, $C_1$-$C_6$ alkyl, $C_1$-$C_6$ alkoxy, halogen or —OH. The aryl group may optionally be fused with one or two cycloalkyl group(s) or other aryl group(s) resulting in polycyclic ring system. The fused group may optionally be substituted with one or more substituents selected from H, $C_1$-$C_6$ alkyl, $C_1$-$C_6$ alkoxy, halogen, haloalkyl or —OH.

The term "heterocyclyl" as used herein refers to a non-aromatic 3 to 14 membered monocyclic cycloalkyl group, fully or partially unsaturated, with one to five heteroatoms independently selected from N, O, S or P. "Heterocyclyl" also includes, but is not limited to, bicyclic or tricyclic rings, wherein the heterocyclyl ring is fused to one or two rings independently selected from the group consisting of an aryl ring, a cycloalkyl ring, a heteroaryl ring or heterocyclyl ring. Examples of heterocyclyl groups include but are not limited to, morpholinyl, oxazolidinyl, tetrahydroiuranyl, tetrahydroquinolinyl, dihydrofuranyl, dihydropyridinyl, dihydroisooxazolyl, dihydrobenzofuryl, azabicyclohexyl, dihydroindonyl, piperidinyl or piperazinyl. The heterocyclyl group may optionally be substituted at any available position with one or more substituents selected from H, $C_1$-$C_6$ alkyl, $C_1$-$C_6$ alkoxy, halogen, haloalkyl or —OH. Point of attachment of heterocyclyl group to another group may be through carbon or heteroatom.

The term "heteroaryl" as used herein refers to a five to ten membered aromatic monocyclic ring structure, containing one to five heteroatoms independently selected from N, O, S or P. "Heteroaryl" also includes, but is not limited to, bicyclic or tricyclic rings, wherein the above defined heteroaryl ring is fused to one or two rings independently selected from the group consisting of an aryl ring, a cycloalkyl ring, a heterocyclyl ring and another monocyclic heteroaryl ring. Examples of heteroaryl groups include, but are not limited to, oxazolyl, imidazolyl, pyrrolyl, 1,2,3-triazolyl, 1,2,4-triazolyl, tetrazolyl, fhiazolyl, oxadiazolyl, quinolinyl, benzoimidazolyl, thiadiazolyl, pyridinyl, pyridazinyl, pyrimidinyl, thienyl, isoxazolyl, triazinyl, furanyl, benzofuranyl, indolyl, benzothiazolyl, benzoxazolyl, imidazo[1,2-a]pyrimidine, imidazo[1,2-a]pyrazine, tetrahydroquinoline and the like. The heteroaryl group may optionally be substituted at any available position with one or more substituents selected from H, $C_1$-$C_6$ alkyl, $C_1$-$C_6$ alkoxy, halogen, haloalkyl or —OH. Point of attachment of heteroaryl group to another group may be through carbon or heteroatom.

The term "halogen" or "halo" as used herein by itself or as part of another group refers to chlorine, bromine, fluorine or iodine and their isotopes. The term "radiohalogen" refers specifically to radioactive halogen isotopes.

The term "haloalkyl" as used herein refers to an alkyl group, as defined above, substituted by one or more halogen, as defined above, for example chloromethyl, iodomethyl, trifluoromethyl, 2,2,2-trifluoroethyl, or 2-chloroethyl.

In one exemplary embodiment of the present invention, $R^6$ is selected from the group consisting of:

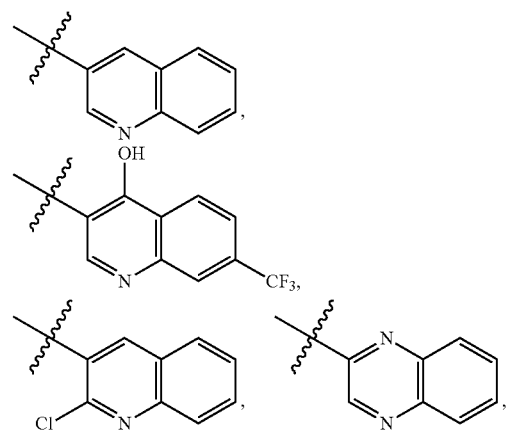

-continued

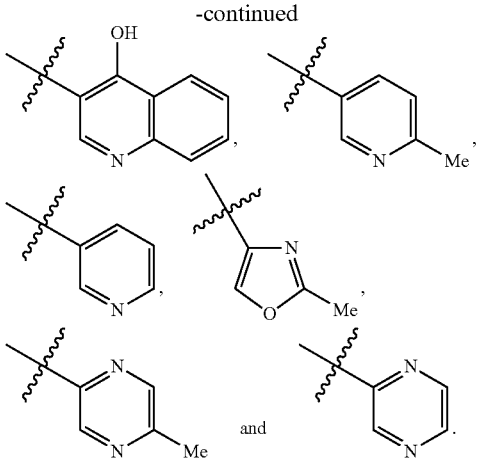

In one embodiment, it is especially preferred that $R^6$ is

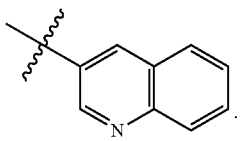 [SMILES: *c1cnc2ccccc2c1]

In another exemplary embodiment, the value of n is from 1 to 4. Most preferably, the value of n is from 1 to 3. It is especially preferred that n is one.

In one exemplary embodiment, the value of p is selected from 0 and 1. It is especially preferred that p is one.

In another exemplary embodiment, $R^7$ and $R^8$ are same or different and independently selected from —OMe or —OEt. It is especially preferred that each of $R^7$ and $R^8$ is —OMe.

Preferred compounds of Formula 1 include those compounds wherein "Q" is a direct bond.

In one embodiment, it is preferred that 'X' can be an radioactive isotope selected from positron-emitting radionuclides such as $^{15}O$, $^{13}N$, $^{11}C$, $^{18}F$, $^{68}Ga$, $^{89}Zr$ and $^{94}Tc$ and gamma-emitting radionuclides are $_{18}F$, $^{99}mTc$, $^{201}Tl$ and $^{123}I$. In another preferred embodiment, "X" can be $^{68}Ga$ (half-life 68 minutes) and can be used as radiotracer in positron emission tomography (PET) imaging in diagnostic applications.

In yet another preferred embodiment, "X" can be $^{94}Tc$ (half-life: 4.883 hours) and can be used as radiotracer in positron emission tomography (PET) imaging in diagnostic applications.

In yet another preferred embodiment, "X" can be $^{89}Zr$ (half-life 78.41 hours) and can be used as radiotracer in positron emission tomography (PET) imaging in diagnostic applications.

In yet another preferred embodiment, "X" can be $^{99}mTc$ (half-life: 6.01 hours) and can be used as radiotracer in positron emission tomography (PET) imaging and SPECT (single photon emission tomography) in diagnostic applications.

In one embodiment, it is especially preferred that "X" is Fluorine and its radioactive isotopes. The preferred radioactive isotope is $^{18}F$. $^{18}F$ is having the longest half life of 109.771 minutes which allows it to serve commercially as an important source of positrons and that is why it is majorly used as radiotracer in positron emission tomography (PET) imaging in diagnostic applications.

In an exemplary embodiment, a compound of Formula 1 is represented by Formula 1a:

Formula 1a

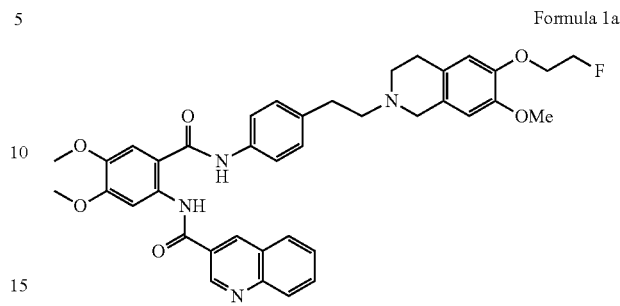

The compounds of the present invention may also contain a radioactive isotope of carbon as the radiolabel. This refers to a compound that comprises one or more radioactive carbon atoms, preferably $^{11}C$, with a specific activity above that of the background level for that atom. It is well known, in this respect, that naturally occurring elements are present in the form of varying isotopes, some of which are radioactive isotopes. The radioactivity of the naturally occurring elements is a result of the natural distribution or abundance of these isotopes, and is commonly referred to as a background level. The carbon labeled compounds of the present invention can have a specific activity that is higher than the natural abundance, and therefore above the background level. The composition claimed herein comprising a carbon-labeled compound(s) of the present invention can have an amount of the compound such that the composition can be used for tracing, imaging, radiotherapy, and the like.

The compounds of Formulae 1 and 1a may also be solvated, especially hydrated. Hydration may occur during manufacturing of the compounds or compositions comprising the compounds, or the hydration may occur over time due to the hygroscopic nature of the compounds. In addition, the compounds of the present invention can exist in un solvated as well as solvated forms with pharmaceutically acceptable solvents such as water, ethanol, and the like.

In general, the solvated forms are considered equivalent to the unsolvated forms for the purposes of the present invention.

Another aspect of this invention is related to methods of preparing a compound of Formula 1.

In one embodiment, the present invention provides novel intermediates of Formula 2 in preparation of compounds of Formula 1.

Formula 2

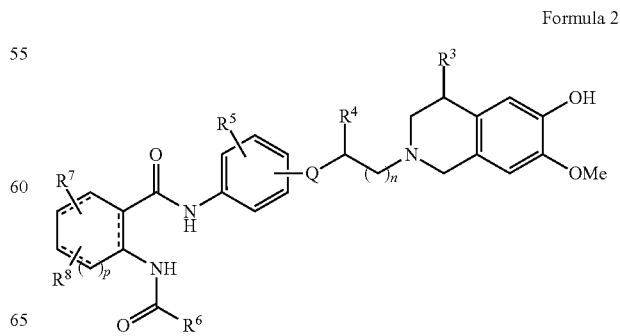

The present invention also provides methods of preparation of intermediates of Formula 2.

In an exemplary embodiment, an intermediate of Formula 2 is represented by Formula 2a:

Formula 2a

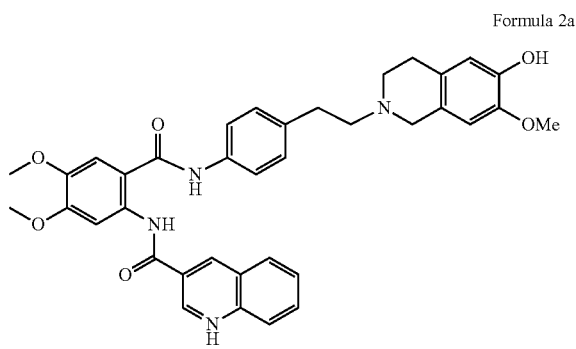 [SMILES: COc1cc2c(cc1O)CCN(CCc1ccc(NC(=O)c3cc(OC)c(OC)cc3NC(=O)c3cnc4ccccc4c3)cc1)C2]

One exemplary embodiment provides the synthesis of a novel intermediate of Formula 2a as shown in a general Scheme 1 below comprising the steps of:

i. Performing O-benzylation of Compound 1 to obtain 3-(benzyloxy)-4-methoxybenzaldehyde (Compound 2).
ii. Performing condensation reaction of 3-(benzyloxy)-4-methoxybenzaldehyde with nitromethane to afford (E)-2-(benzyloxy)-1-methoxy-4-(2-nitrovinyl)benzene (Compound 3).
iii. Carrying out reduction of (E)-2-(benzyloxy)-1-methoxy-4-(2-nitrovinyl)benzene to obtaining 2-(3-(benzyloxy)-4-methoxyphenyl)ethanamine (Compound 4).
iv. Preforming cyclisation reaction of 2-(3-(benzyloxy)-4-methoxyphenyl)ethanamine with paraformaldehyde and formic acid to obtain Compound 5.
v. Performing N-Alkylation of Compound 5 with 1-(2-bromoethyl)-4-nitrobenzene to form 7(benzyloxy)-6-methoxy-2-(4-nitrophenethyl)-1,2,3,4-tetrahydroisoquinoline (Compound 6).
vi. Performing Reduction of Compound 6 to form 2-(4-aminophenethyl)-6-methoxy-1,2,3,4-tetrahydroisoquinolin-7-ol (Compound 7).
vii. Performing Amidation of Compound 7 with 3,4-dimethoxybenzoyl chloride to form N-(4-(2-(6-hydroxy-7-methoxy-3,4-dihydroisoquinolin-2(1H)-yl)ethyl)phenyl)-4,5-dimethoxy-2-nitrobenzamide (Compound 8).
viii. Performing reduction of Compound 8 to form 2-amino-N-(4-(2-(6-hydroxy-7-methoxy-3,4-dihydroisoquinolin-2(1H)-yl)ethyl)phenyl)-4,5-dimethoxybenzamide (Compound 9).
ix. Performing Amidation of Compound 9 with Compound 10 to obtain an intermediate of Formula 2a.

Scheme I

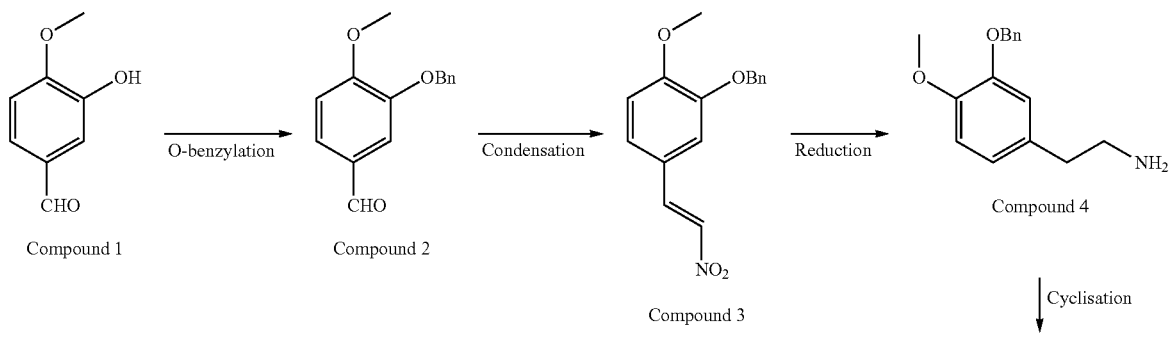

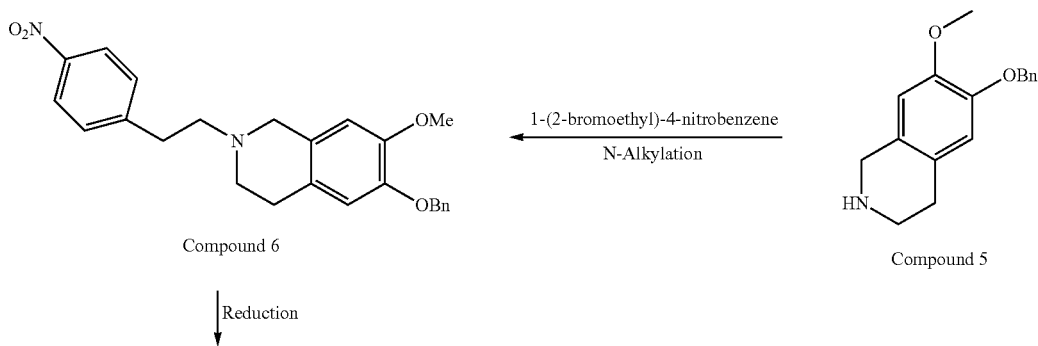

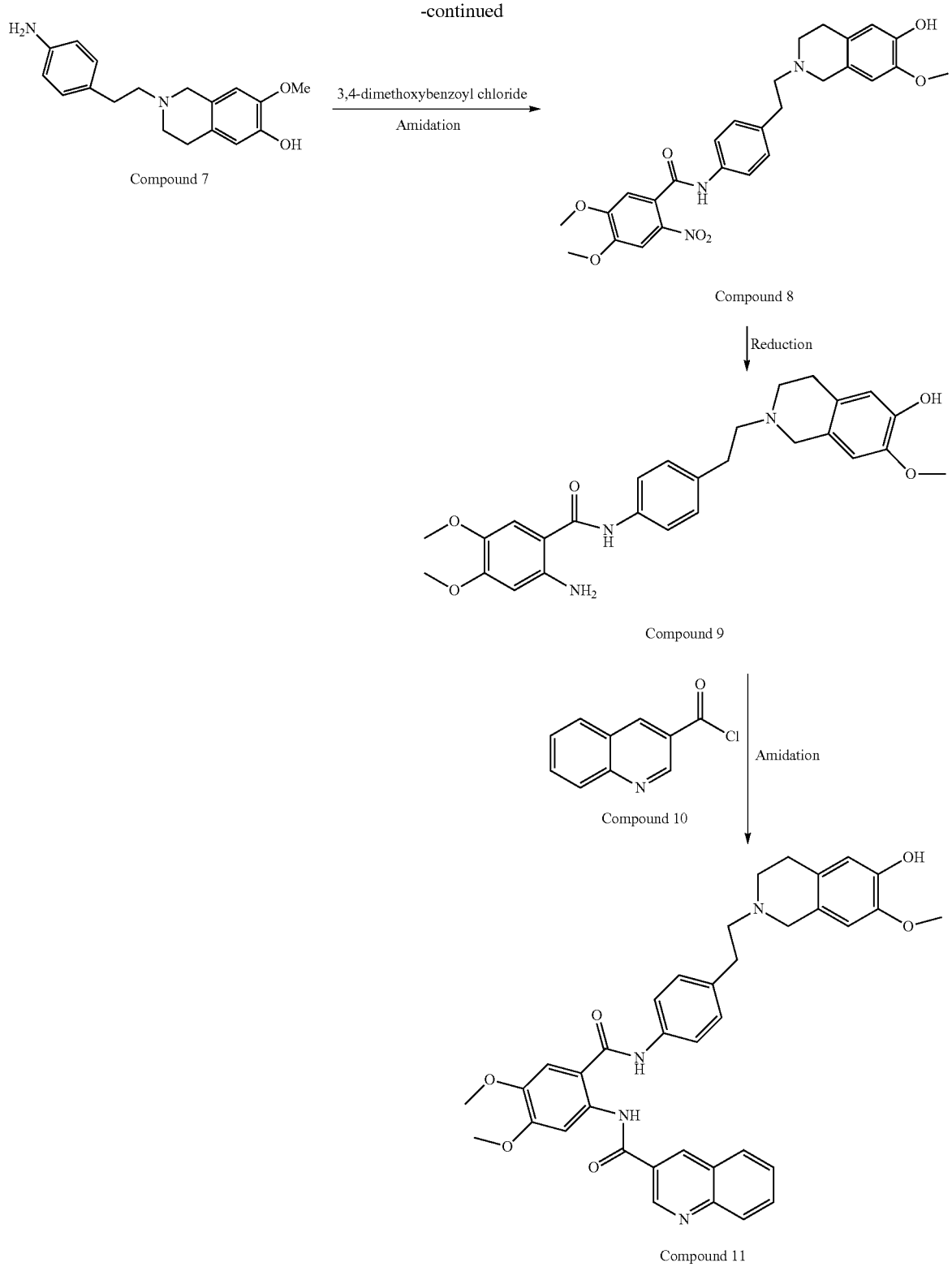

O-benzylation of Compound 1 can be carried out in presence of one or more bases selected from but not limiting to potassium carbonate, NaOH, KOH, sodium carbonate, sodium hydride and the like, and in presence of one or more solvents selected from but not limited to methanol, DMF, DMSO and the like.

Condensation reaction of Compound 2 can be carried out in presence of Acetic acid and ammonium acetate, and in presence of one or more solvents selected from but not limited to DMF, DMSO, acetamide and the like.

Reduction of Compound 3 can be carried out in presence of a reducing agent selected from but not limiting to lithium aluminium hydride, lithium selectride and the like, and in presence of one or more solvents selected from but not limited to methanol, THF, dioxane and the like.

Cyclisation reaction of Compound 4 can be carried out in presence of one or more suitable bases selected from but not limited to DMF, DMSO, acetamide and the like.

N-alkylation of Compound 5 can be carried out in presence of one or base selected from but not limiting to NaOH, KOH, CsCo₃, calcium hydroxide, Triethylamine (TEA), Pyridine (PY), collidine, and in presence of one or more suitable hydroxylic solvents.

Reduction of Compounds 6 and 8 can be carried out in presence of one or more reducing agents selected from but not limiting to 10% Pd/C, Sodium bisulphate, Sodium disulfide, Sodium dithionite, Ammonium formate, RaNi and the like.

Amidation of Compounds 7 and 9 can be carried out in presence of one or more solvents selected from but not limiting to DCM, pyridine and the like.

A further embodiment of the present invention provides preparation of a novel compound of 1a comprising the step of reacting intermediate of Formula 2a with iodofluoro ethane in presence of cesium carbonate and DMF.

In a novel radiolabeled compound of Formula 1, X is preferably $^{18}F$. More preferably, a radiolabeled compound of Formula 1 is represented as a compound of Formula 1b as shown below:

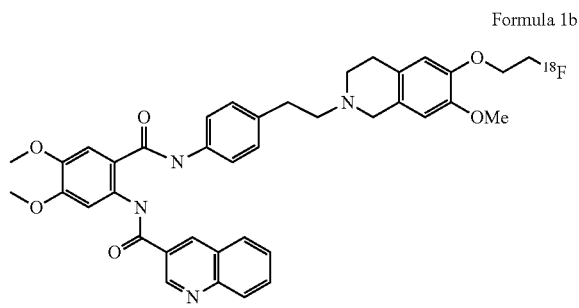 [SMILES: COc1cc(NC(=O)c2cnc3ccccc3c2)c(C(=O)Nc2ccc(CCN3CCc4cc(OCC[18F])c(OC)cc4C3)cc2)cc1OC]

Formula 1b

The present invention also provides diagnostic compositions comprising a radiolabeled compound of Formula 1 and a pharmaceutically acceptable carrier or diluent.

$^{18}F$-fluoride can be produced by the various techniques known in the art, for example, in one of the embodiments of the present invention, $^{18}F$-fluoride can initially be produced as fluoride anion in a cyclotron by proton bombardment. The fluoride anion is then chemically introduced in X—CH2-CH2-L where X=halogen or tosyl to form $^{18}F$—CH₂CH₂-L, where L represents a leaving group expected to depart once a nucleophile attacks in a chemical reaction. During an insertion reaction, 6-hydroxy group in the isoquinoline portion of compound of Formula 1a attacks $^{18}F$—CH₂CH₂-L to replace L to form labeled compound of formula 1b In one exemplary embodiment of the present invention, "L" can be a tosyl group.

In some embodiments, the present invention is directed to methods for determining the clinical efficacy or the metabolic behavior of the subject when exposed to a compound of Formula 1, the method can comprise the steps of: (a) administering a first quantity of a radiolabeled compound of Formula 1 to a subject; (b) detecting a signal from an in situ sensor, the signal corresponding to the radiation emitted by the radiolabeled compound of Formula 1 in a region of interest in the subject; (c) relaying the signal to a location external of the subject's body; (d) repeating said detecting and relaying steps over periodically or at different time intervals in general or say at least about 0.25-24 hours; and (e) monitoring the signals over time.

In certain embodiments, the monitoring step can be used to determine the metabolic and/or biokinetic response of the subject to thereby predict or assess the in vivo clinical efficacy or local tissue sensitivity to a therapeutic dose of a compound of Formula 1 prior to administration thereof.

The administrating step can be carried out in vivo and performed such that the radiolabeled compound of Formula 1 is either delivered locally to the region of interest (such as via injection) or such that the radiolabeled compound of Formula 1 is delivered systemically (such as through a syringe or an intravenous catheter). The radiolabeled compound of Formula 1 can be provided as a first quantity amount which is less than a therapeutic quantity of a corresponding non-radiolabeled compound of Formula 1.

Other embodiments of the present invention are directed to a detection system for detecting radiation emitted from an internally administered radiolabeled compound of Formula 1. The system includes at least one radiation sensor configured for in vivo operation. The sensor is configured to detect gamma radiation emitted from a radiolabeled compound of Formula 1 or its biochemical constituents, in or proximate targeted localized tissue in the body. The sensor is configured to detect emitted gamma radiation, at least intermittently, over a period of time extending from about 0.25-24 hours (the evaluation period can be proximate in time to and at least before each of a plurality of planned therapeutic treatments which are administered temporally separate from each other). The system also includes a processor operably associated with (each of) the radiation sensor(s). The processor is configured to receive signal data associated with the detected radiation from the sensor. The processor includes computer program code for monitoring selected in vivo parameters associated with time-dependent measurement profile and/or the uptake and/or retention of the radiolabeled compound of Formula 1 in the targeted localized tissue.

One embodiment of the present invention provides a radiolabeled novel compound of Formula 1 as a radiotracer for target detection and quantitative imaging of P-glycoprotein. In some embodiments, the present invention provides a method for target detection and quantitative imaging of P-glycoprotein to detect MDR pathology and assign MDR 1/P-gp as the cause of drug resistance in cancer subjects exhibiting disease progression or impairment due to failure of chemotherapy to enable for patients stratification based on therapeutic response and guidance to design a bio-marker specific treatment regime and ensure unnecessary toxicities and improve survival outcomes and overall quality of life for the patient. Thus the present invention concerning the use of a radiolabeled compound of Formula 1 for imaging P-gp function in vitro and in vivo provides an aid in the diagnosis of MDR disorders such as in cancers e.g. brain cancer, breast cancer, bone cancer, etc. and other solid tumors and neurological disorders of the central nervous system such as Parkinson disease, Alzheimer disease, etc.

In one embodiment of the present invention, the novel compound of Formula 1 can be used as substrate for at least one ABC transporter selected from Pgp, MRP1 or BCRP and may have activity as inhibitor of ABC transporter and thus may be used as modulator of MDR in the treatment of MDR cancers.

In an embodiment of the present invention, the compound of Formula 1 can be used to modulate transporter activity and substrate specificity of at least one ABC transporter selected from Pgp, MRP1 or BCRP in chemotherapeutic applications.

The compound of Formula 1 as disclosed herein can be used in a method of treating a disease which presents ABC transporter mediated MDR, comprising administering a therapeutically effective amount of the compound of the present invention to a subject in need thereof.

In another embodiment of the present invention, the compound of Formula 1 can modulate the efflux capability of at least one ABC transporter selected from Pgp, MRP1 or BCRP, in a cell or tissue by contacting the cell or tissue with a chemotherapeutic agent that promotes or inhibits efflux attributed to the ABC transporter, and wherein activity of the ABC transporter through gene expression is unaffected.

In another embodiment of the present invention, the compound of Formula 1 can be administered along with chemotherapeutic agents to potentiate the cytotoxicity of the chemotherapeutic agents for treatment of a human or animal patient harbouring a tumour. Such drugs include many anti-cancer drugs and cytotoxic agents, such as vinca alkaloids, anthracyclines, epipodophyllotoxins, taxanes, actinomycins, colchicine, puromycin, toxic peptides (e.g., valinomycin), topotecan, and ethidium bromide (See, Pastan and Gottesman, 1987, New England J Med 316(22):1388-1393).

The compound of Formula 1 as disclosed herein contacted with a therapeutic drug in a cell or tissue can activate or inhibit the efflux capability of the ABC transporter to potentiating the activity of therapeutic drug without affecting the gene expressing activity of the ABC transporter.

The compound of Formula 1 can be used to selectively inhibit the efflux capability of the ABC transporter to retain a therapeutic drug, like a chemotherapeutic drug or antibiotic drug in the cell, while maintaining normal efflux capabilities with respect to other compounds.

The compound of Formula 1 can be used to selectively maintain normal efflux capability of the ABC transporter with respect to all compounds except a therapeutic drug, like a chemotherapeutic drug.

In one embodiment of the present invention, the compound of Formula 1 can be used to provide a method of facilitating detoxification of a cell or tissue by contacting the cell or tissue with the compound of Formula 1 that increases the efflux capability of an ABC transporter, wherein activity of the ABC transporter through gene expression is unaffected. In particular, the efflux capability of the ABC transporter is selectively increased with respect to eliminating a predetermined toxin, e.g., a carcinogen, while maintaining normal efflux capabilities with respect to other compounds in the cell.

In another embodiment of the present invention, the compound of Formula 1 can be used to provide a method of modulating the efficacy of a blood-brain barrier or placental barrier comprising administering to an individual in need thereof a therapeutically effective amount of the compound of Formula 1 capable of modulating the activity of an ABC transporter, wherein activity of the ABC transporter through gene expression is unaffected.

In another embodiment of the present invention, the compound of Formula 1 can be used to reduce the efficacy of the blood-brain barrier or placental barrier. In this embodiment, barrier efficacy is selectively reduced with respect to a predetermined compound, e.g., a therapeutic drug, while maintaining normal barrier efficacy with respect to other compounds. In another embodiment, the efficacy of the blood-brain or placental barrier is increased. In this embodiment, barrier efficacy is selectively increased with respect to a predetermined compound, e.g., an acute or chronic toxin, while maintaining normal efflux efficacy with respect to other compounds.

The term "pharmaceutically acceptable carrier or diluent" as used herein can include one or more from: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, diagnostic compositions of the present invention are non-pyrogenic, i.e., do not induce significant temperature elevations when administered to a patient.

The term "pharmaceutically acceptable salt" as used herein refer to e salts which can be prepared in-situ during final isolation and purification or by separately reacting a purified compound in its free base form with a suitable organic or inorganic acid, and isolating the salt thus formed. The representative pharmaceutical acceptable salts can include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, dimesylate, glucoheptonate, lactobionate, laurylsulphonate salts, and amino acid salts, and the like. In one embodiment of the present invention, a compound of Formula 1 can contain one or more acidic functional groups and, thus, are capable of forming pharmaceutically acceptable salts with pharmaceutically acceptable bases.

In another embodiment of the present invention, a compound of Formula 1 can be incorporated with wetting agents, emulsifiers, and lubricants, such as sodium lauryl sulfate and magnesium stearate, as well as coloring agents, release agents, coating agents, sweetening, flavoring, and perfuming agents, preservatives and antioxidants.

In some embodiments of the present invention, a compound of Formula 1 can be administered orally, intravenously through injections or implanted in the target area.

In some embodiments of the present invention, a compound of Formula 1 can be administered to the subject in a therapeutic dosage which is at least about 1.5 to 2 times of the dose which is used for diagnostic and imaging purposes. In another embodiment, a compound of Formula 1 can be administered to the subject in the maximum dosage that the subject can tolerate. In another embodiment, the compound of Formula 1 can be administered in a dosage of about 30 to 100 mCi per 50 kg of body weight.

In another embodiment of the invention, a compound of Formula 1 can be administered in conjunction with any combination of immunotherapy, surgery, radiation therapy, or other chemotherapy to the subject at any stage in the treatment of the subject.

In an embodiment of the present invention, the radiolabeled compounds of Formula 1 can be used to treat diseases by administration of radiolabeled compounds in dosages significantly higher than those used for diagnostic and imaging purposes.

The invention is explained in detail in the following examples which are given solely for the purpose of illustration only and therefore should not be construed to limit the scope of the invention. All of the starting materials are either commercially available or can be prepared by procedures that would be well known to one of ordinary skill in organic chemistry. Solvents were dried prior to use wherever necessary by standard methods (Perrin, D. D.; Armarego, W. L. F. Purification of Laboratory Chemicals, Pergamon Press: Oxford, 1988).

The compounds prepared in Examples 1 to 11 were characterized by 1H NMR and mass spectroscopic techniques. 1H NMR spectra were obtained on a Varian 400 MHz spectrometer in $CDCl_3$ or DMSO. Chemical shifts are reported as δ values in parts per million (ppm), relative to TMS as internal standard. AU coupling constants (J) values are given in Hz. Mass spectra (MS) were recorded on LC 2010 shimadzu instrument.

EXAMPLES

The present disclosure is further explained in the form of following examples. However, it is to be understood that the foregoing examples are merely illustrative and are not to be taken as limitations upon the scope of the invention. Various changes and modifications to the disclosed embodiments will be apparent to those skilled in the art. Such changes and modifications may be made without departing from the scope of the invention.

Example 1

Preparation of 3-(benzyloxy)-4-methoxybenzaldehyde (Compound 2)

A stirred solution of Compound 1 (250 g, 1.645 mmol, 1 eq) in methanol (3 L), at rt was added to potassium carbonate (340.4 g, 2.467 mmol, 1.5 eq), and sodium iodide (24.7 g, 0.164 mmol, 0.1 eq) and benzyl chloride (246 mL, 2.138 mmol, 1.3 eq). The reaction mixture was stirred for 20 minutes and heated to reflux (60-65° C. internal temperature) and maintained for 16 h reflux. The reaction progress was monitored by TLC, and continued till complete consumption of Compound 1. The reaction mixture was then cooled to rt and quenched with ice cold water (7 L) and gummy liquid was formed. The water layer was decanted. After that, water (2 L) was added to the reaction mixture and stirred for 2 h and filtered. The compound was washed with methanol (500 mL) and pet ether (2×500 mL). The compound obtained was dried. The final compound obtained was Compound 2 (1125 g, 94.8%) as a white solid (TLC system: 50% CHCl3/pet ether, Rf: 0.8). $^1$H-NMR (400 MHz, $CDCl_3$): 9.8 (s, 1H), 7.49-7.42 (m, 4H), 7.40 (t, J=7.2Hz, 3H), 7.22 (d, J=7.6 Hz, 1H), 6.98 (d, J=8.4 Hz, 1H), 5.19 (m, 2H), 3.96 (s, 3H).

Example 2

Preparation of (E)-2-(benzyloxy)-1-methoxy-4-(2-nitrovinyl)benzene (Compound 3)

A solution of compound 2 (385 g, 1.591 mmol, 1 eq) in acetic acid (2.5 L, 10 v), at rt, was added to ammonium acetate (306.5 g, 3.977 mmol, 2.5 eq), and stirred for 15 minutes. Nitromethane (255.5 mL, 4.773 mmol, 3 eq) was then added in drop wise manner at rt to this solution till the colour changes from colorless to light yellow. After completion of addition of nitromethane, the reaction mixture was stirred for 30 minutes at rt and heated to reflux (105-115° C. inner temperature). The reaction mixture was refluxed for 4 h, and filtered. The solid was washed with constant stirring in methanol for 30 min and filtered. The compound was then washed with pet ether (2×1 L) dried. The final compound obtained was Compound 3 (405 g, 89.3%) as white solid (TLC system: 50% CHCl3/DCM, Rf: 0.8). $^1$H-NMR (400 MHz, DMSO-$d_6$): 8.2 (d, J=13.6 Hz, 1H), 8.07 (d, J=13.6 Hz, 1H), 7.64 (d, J=1.6 Hz, 1H), 7.47-7.34 (m, 6H), 7.09 (d, J=8.8 Hz, 1H), 5.33 (s, 2H), 3.83 (s, 3H). LCMS purity: 99.43% at 214 nm and 99.9% at 254 nm (Zodiac C-18 (150×4.6) mm, 3.5 micron, Mobile Phase A 0.01M aq. $NH_4OAc$, B=$CH_3CN$; Gradient (T/%B): 0/10, 10/90, 15/90, 15.1/10; Flow; 0.8 ml/min, $R_t$=10.89 min; Diluent: $CH_3CN$); Mass (m/z)=284.1 (APCI, −ve mode).

Example 3

Preparation of 2-(3-(benzyloxy)-4-methoxyphenyl)-ethanamine (Compound 4)

A stirred solution of compound 3 (400 g, 1.403 mmol, 1 eq) in dry THF (3 L) was added to suspension of lithium aluminum hydride (80 g, 2.10 mmol, 1.5 eq) in THF (1 L) drop by drop at −30° C. to −10° C. while ensuring that inner temperature of the reaction should not go above −10° C. After completion of addition of the starting material, the reaction mixture was slowly warmed to rt and stirred for 20 h at rt. The reaction progress was monitored by TLC, showed complete consumption of compound 3. The reaction mixture was cooled to −30° C. After that, water (80 mL), 15% NaOH aq. solution (80 mL) and water (240 mL) were added to reaction mixture drop by drop while always maintaining internal temp −10° C. Thereafter reaction mixture was warmed to rt. and stirred for 3 h to ensure quenching of excess LiAlH4. The reaction mixture was then filtered over celite bed. The solid was washed with THF (5 L). The combined organic layer were concentrated. The final compound obtained was compound 4 (405 g, 89.3%) as brown gummy liquid (TLC system: 10% MeOH/CHCl3), Rf: 02). $^1$H-NMR (400 MHz, DMSO-$d_6$): 7.44-7.33 (m, 5H), 6.89 (br. d, J=8.8 Hz, 1H), 6.76 (dd, J=8.4, 2.0 Hz, 1H), 5.04 (s, 2H), 3.72 (s, 3H), 2.73 (t, J=6.8 Hz, 2H), 2.53 (t, J=6.8 Hz, 2H). LCMS purity: 67.7% at 214 nm and 50.32% at 254 nm (Zodiac C-18 (150×4.6) mm, 3.5 micron, Mobile Phase A 0.01M aq. $NH_4OAc$, B=$CH_3CN$; Gradient (T/% B): 0/10, 10/90, 15/90, 15.1/10; Flow; 0.8 ml/min, $R_t$=6.89 min; Diluent: $CH_3CN$+MeOH); Mass (m/z)=258.1 (APCI, +ve mode).

Example 4

Preparation of 6-benzyloxy-7-methoxy-1,2,3,4-tetra-hydroisoquinoline (Compound 5)

A stirred solution of Compound 4 (575 g, 2.237 mmol, 1 eq) in formic acid (2.3 L) was added to paraformaldehyde. The temperature of the reaction mixture slowly rises to 40-45° C. The reaction mixture was stirred for 4 h and progress was monitored by TLC till it showed complete consumption of Compound 4. The reaction mixture was quenched with ice cold water (15 L) and basified to pH=7-8 with solid NaHCO$_3$. The aqueous layer was extracted with ethyl acetate (5×1 L) and dried (Na$_2$SO$_4$) and filtered and concentrated. Then ethyl acetate (1 L) was added to the crude obtained and stirred for 2 h. The reaction mixture was then filtered and washed with ethyl acetate (2×100 mL) and dried. The final compound obtained was Compound 5 (78 g, 13%) as white solid (TLC system: 10% MeOH/CHCl3, Rf: 0.21). $^1$H-NMR (400 MHz, DMSO-d$_6$): 7.44-7.29 (m, 5H), 6.75 (br. s, 1H), 6.67 (s, 1H), 5.01 (s, 2H), 3.69 (s, 3H), 3.56 (s, 2H), 2.70 (br. s, 4H). Mass (m/z)=270.1 (APCI, +ve mode).

Example 5

Preparation of 7-(benzyloxy)-6-methoxy-2-(4-nitrophenethyl)-1,2,3,4-tetrahydroisoquinoline(Compound 6)

A stirred solution of Compound 5 (78 g, 0.29 mmol, 1 eq) in methanol (1.6 L, 20 v), at rt, was added to potassium carbonate (60 g, 0.43 mmol, 1 eq), sodium iodide (43.4 g, 0.29 mmol, 1 eq) and stirred for 15 minutes. Then 1-(2-bromoethyl)-4-nitrobenzene was added at rt. The reaction mixture was then heated to 65 °C-70° C. and stirred for 20 h. The reaction mixture was cooled to rt and poured in ice cold water (10 L). The aqueous layer was extracted with ethyl acetate (3×1 L). The combined organic layer was washed with brine (1 L) and dried (Na$_2$SO$_4$). After filtering and concentration of the resulting mixture, a brown gummy liquid was obtained. To this, ethanol (100 mL) was added and then sonicated for 30 min and kept at room temperature for 20 h. The formed compound was filtered and washed with methanol (10 mL), then dried. The final compound obtained was Compound 6 (75 g, 61.9%) as white solid (TLC system: 10% MeOH/CHCl3, Rf: 0.6). 8.19 (br. d, J=8.4 Hz, 2H), 7.56 (br. d, J=8.4 Hz, 2H), 7.49-7.06 (m, 5H), 6.75 (s, 1H), 6.64 (s, 1H), 5.04 (s, 2H), 3.72 (s, 3H), 3.53 (s, 2H), 2.92 (t, J=6.8 Hz, 2H), 2.73 (t, J=6.8 Hz, 2H), 2.67 (s, 2H). LCMS purity: 95.5% at 214 nm and 98.28% at 254 nm (Zodiac C-18 (150×4.6) mm, 3.5 micron, Mobile Phase A 0.01M aq. NH$_4$OAc, B=CH$_3$CN; Gradient (T/% B): 0/10, 10/90, 15/90, 15.1/10; Flow; 0.8 ml/min, Diluent: CH$_3$CN); R$_t$=8.3 min Mass (m/z)=419.1 (APCI, +ve mode) and 417.1 (APCI, −ve mode).

Example 6

Preparation of 2-(4-aminophenethyl)-6-methoxy-1,2,3,4-tetrahydroisoquinolin-7-ol (Compound 7)

A solution of Compound 6 (45 g, 0.108 mmol, 1 L) in methanol (150 mL) and THF (625 mL,) (Argon purged for 1 h), at rt, were added to 10% Pd/C (Wet) (15 g, 33% w/w) in a parr shaker ss vessel. The reaction mixture was hydrogenated under 90 PSI H$_2$ pressure for 20 h at rt. The reaction mixture was then filtered over celite bed and washed with 1:1 mixture of methanol in THF (200 mL×6) till TLC showed complete absence of desired compound. The combined organic layer was concentrated and the obtained crude was stirred in methanol (100 mL) for 30 min, filtered and dried. The final compound obtained was Compound 7 (24.7 g, 77%) as white solid (TLCsystem: 10% MeOH/CHCl3, Rf: 0.3). $^1$H-NMR (400 MHz, DMSO-d$_6$): 8.66 (s, 1H), 6.89 (d, J=8.4 Hz, 2H), 6.58 (s, 1H), 6.48 (overlapped d, J=8.4 Hz, 2H), 6.47 (s, 1H), 4.80 (br. hump, 2H), 3.69 (s, 3H), 3.47 (s, 2H), 2.62 (br. s, 6H), 2.56 (s, 2H). LCMS purity: 98.6% at 214 nm and 99.1% at 254 nm (Zodiac C-18 (150×4.6) mm, 3.5 micron, Mobile Phase A 0.01M aq. NH$_4$OAc, B=CH$_3$CN; Gradient (T/%B): 0/10, 10/90, 15/90, 15.1/10; Flow; 0.8 ml/min, Diluent: CH$_3$CN); R$_t$=5.69 min; Mass (m/z)=299.1 (APCI, +ve mode).

Example 7

Preparation of N-(4-(2-(6-hydroxy-7-methoxy-3,4-dihydroisoquinolin-2(1H)-yl)ethyl)phenyl)-4,5-dimethoxy-2-nitrobenzamide (Compound 8)

A solution of Compound 7 (40 g, 0.134 mmol, 1 eq) in Toulene (500 mL), at rt, was added to thionyl chloride in drop by drop and stirred for 30 minutes and slowly heated to 100° C. Catalytic amount of DMF was added to reaction mixture in drop wise manner and stirred for 2 h at 100° C. The reaction mixture was formed as clear solution. After getting clear solution small aliquot from reaction was quenched in methanol and reaction progress was monitored by TLC, till complete acid chloride formation. The reaction mixture was cooled to rt and concentrated. This acid chloride was dissolved in DCM (300 mL) and to this was added a solution of Compound 7 and pyridine in DCM at 0° C. in drop wise manner. After completion of addition, the reaction mixture was slowly warmed to rt and stirred for 2 h. The reaction mixture was then quenched with saturated NaHCO$_3$, aqueous solution (1 L) and concentrated. The obtained solid was filtered and washed with water (250 mL×2). This solid was dissolved in DCM (5 L), dried (Na$_2$SO$_4$), filtered and concentrated. The crude compound was triturated with 10% acetone in ethyl acetate (2×250 mL), filtered and dried. The final compound obtained was compound 8 (40 g, 59%) as yellow solid (TLC system: 10% MeOH/CHCl3, Rf: 0.41). $^1$H-NMR (400 MHz, CDCl$_3$, data reported for major compound, impurity of diacylated compound m/z 719 (+ve mode) is observed): 10.44 (s, 1H), 8.67 (s, 1H), 7.57 (s, 1H), 7.55(d, J=8.0 Hz, 2H), 7.22 (overlapped d, J=8.4 Hz, 2H), 6.56 (s, 1H), 6.51 (s, 1H), 4.02 (d, J=8.0Hz, 1H), 3.96 (d, J=8.0 Hz, 1H), 3.91 (s, 3H), 3.89 (s, 3H), 3.69 (s, 3H), 2.76-2.56 (series of m, 8H). LCMS purity: 62.8% at 214 nm and 67.7% at 254 nm (Gemini C-18 (50×4.6) mm, 3.5 micron, Mobile Phase A 0.01M aq. NH$_4$OAc, B=CH$_3$CN; Gradient (T/% B): 0/40, 5/80, 8/90, 12/90, 12.1/40; Flow; 0.7 ml/min, Diluent: CH$_3$CN); R$_t$=3.1 min; Mass (m/z)=508.1 (APCI, +ve mode).

Example 8

Preparation of 2-amino-N-(4-(2-(6-hydroxy-7-methoxy-3,4-dihydroisoquinolin-2(1H)-yl)ethyl)phenyl)-4,5-dimethoxybenzamide (Compound 9)

A solution of Compound 8 (40 g, 78.864 mmol, 1 eq) in 1:1 mixture of methanol in THF (Argan purged for 1 h), at rt, was added 10% Pd/C (wet) (20 g, 50% w/w) in parr shaker vessel. The reaction mixture was hydrogenated for 24 h under 90 PSI H2 Pressure. The reaction mixture was filtered through celite bed and washed with 1:1 mixture of methanol in THF (3×500 mL), methanol (5×250 mL). The combined organic layer was concentrated and filtered with ethyl acetate (100 mL), methanol (1×100 mL) again ethyl acetate (100 mL) and dried. The final compound obtained was compound 9 (30 g, 79%) as off-white solid (TLC system: 10% MeOH/CHCl3), Rf0.41). $^1$H-NMR (400 MHz, DMSO-d$_6$, data reported for major compound): δ 9.66 (s, 1H), 8.67 (s, 1H), 7.57 (d, J=8.0 Hz, 2H), 7.22 (overlapped d, J=8.4 Hz, 2H), 7.21 (s, 1H), 6.58 (s, 1H), 6.48 (s, 1H), 6.36 (s, 1H), 6.29 (br. s, 2H), 3.88-3.80 (m, 2H), 3.73 (s, 3H), 3.72 (s, 3H), 3.70 (s, 3H), 3.51 (s, 3H), 2.76- 2.57 (series of m, 8H). LCMS purity: 88.16% at 214 nm and 89.06% at 254 nm (Gemini C-18 (50×4.6) mm, 3.5 micron, Mobile Phase A 0.01M aq. NH$_4$OAc, B=CH$_3$CN; Gradient (T/% B): 0/30, 4/80, 8/80, 8.1/30; Flow; 0.6 ml/min, Diluent: CH$_3$CN); R$_t$=2.99 min; Mass (m/z)=508.1 (APCI, +ve mode).

Example 9

Preparation of N-(2-((4-(2-(6-hydroxy-7-methoxy-3,4-dihydroisoquinolin-2(1H)-yl)ethyl)phenyl)carbamoyl)-4,5-dimethoxyphenyl)quinoline-3-carboxamide (Formula 2a)

A solution of Compound 10 (30 g, 0.063 mmol, 1 eq), at 0° C. was added to Compound 9 (30 g, 0.063 mmol) and pyridine (25.3 mL, 0.314 mmol,) in dry DCM (1.2 L) in drop wise manner. The reaction mixture was stirred for 20 h at rt. The reaction mixture was then quenched with saturated NaHCO$_3$ (500 mL) solution. The layers were separated. The aqueous layer was extracted with DCM (3×1 L). The combined organic layer was washed with brine (500 mL), dried (Na2SO4), filtered and concentrated. The obtained compound was triturated with methanol (5×100 mL), filtered and dried. The obtained compound was washed with hot methanol (100 mL), filtered and dried. The final compound obtained was compound of Formula 2a (15 g, 37.7%) as yellow solid (TLC system: 10% MeOH/CHCl3), Rf: 0.4). $^1$H-NMR (400 MHz, DMSO-d$_6$): δ 10.43 (s, 1H), 9.33 (d, J=2.4 Hz, 1H), 9.10 (br. s, 1H), 8.88 (d, J=2.4 Hz, 1H), 8.22 (s, 1H), 8.15 (d, J=8.0 Hz, 1H), 8.13 (d, J=8.4 Hz, 1H), 7.92 (t, J=8.4 Hz, 1H), 7.72 (t, J=8.4 Hz, 1H), 7.62 (overlapped d, J=8.4 Hz, 2H), 7.54 (s, 1H), 7.29 (d, J=8.4 Hz, 2H), 6.69 (s, 1H), 6.59 (s, 1H), 6.36 (s, 1H), 6.29 (br. s, 2H), 4.10 (br. hump, 2H), 3.89 (s, 3H), 3.88 (s, 3H), 3.72 (s, 3H), 3.20-2.86 (series of m, 8H). LCMS purity: 96.15% at 214 nm and 96.05% at 254 nm (Gemini C-18 (50×4.6) mm, 3.5 micron, Mobile Phase A 0.01M aq. NH$_4$OAc, B=CH$_3$CN; Gradient (T/%B): 0/30, 4/80, 8/80, 8.1/30; Flow; 0.6 ml/min, Diluent: CH$_3$CN); R$_t$=4.39 min; Mass (m/z)=633.2 (APCI, +ve mode).

Example 10

Preparation of N-(2-((4-(2-(6-(2-fluoroethoxy)-7-methoxy-3,4-dihydroisoquinolin-2(1H)-yl)ethyl)phenyl)carbamoyl)-4,5-dimethoxyphenyl)quinoline-3-carboxamide (Formula 1a)

A solution of compound of Formula 2a (9.9 g, 15.66 mmol, 1 eq) in dry DMF, at rt, was added to cesium carbonate (10.1 g, 31.329 mmol, 2 eq) and stirred for 10 minutes. Then iodofluoro ethane (817 g, 4.7 mmol, 0.3 eq) was added and stirred for 10 min at rt. The reaction mixture was heated to 60° C. to 65° C. Reaction progress was monitored by TLC, till it showed complete consumption of the compound of Formula 2a. The reaction mixture was quenched in ice cold water (700 mL), and stirred for 30 min. The reaction mixture was filtered, washed with water (100 mL), dried. The solid was dissolved in ethyl acetate (500 mL), dried (Na2SO4), filtered and concentrated The obtained compound was triturated with methanol (200 mL), filtered, washed with methanol (50 mL) and dried. This compound was again triturated with ethyl acetate (200 mL), filtered and dried. The final compound obtained was compound of Formula 1a (8.4 g, 79.2%) as pale yellow solid (TLC system: 10% MeOH/CHCl3), Rf: 0.5). $^1$H-NMR (400 MHz, DMSO-d$_6$): 10.31 (s, 1H), 9.34 (d, J=2.4 Hz, 1H), 8.87 (s, 1H), 8.26 (s, 1H), 8.15 (d, J=8.0 Hz, 1H), 8.12 (d, J=8.4 Hz, 1H), 7.92 (t, J=8.4 Hz, 1H), 7.72 (t, J=8.4 Hz, 1H), 7.61 (d, J=8.4 Hz, 2H), 7.52 (s, 1H), 7.29 (d, J=8.4 Hz, 2H), 6.68 (s, 1H), 6.66 (s, 1H), 4.77-4.63 (m, 2H), 4.19-4.09 (m, 2H), 3.88 (s, 3H), 3.87 (s, 3H), 3.72 (s, 3H), 3.52 (s, 2H), 2.80-2.61 (series of m, 8H). LCMS purity: 98.49% at 214 nm and 98.57% at 254 nm (Gemini C-18 (50×4.6) mm, 3.5 micron, Mobile Phase A 0.01M aq. NH$_4$OAc, B=CH$_3$CN; Gradient (T/% B): 0/30, 4/80, 9/80, 9.1/30; Flow; 0.6 ml/min, Diluent: CH$_3$CN); R$_t$=5.14 min; Mass (m/z)=679.2 (APCI, +ve mode) and 677.1 (APCI, −ve mode).

Example 11

Preparation and purification of compound of formula 1b:

Cyclotron:
$^{18}$F-fluoride was produced at a PET trace cyclotron (GE Healthcare, USA) by proton bombardment (E$_p$ 16.7 MeV, 30 min at 50 mA) of 2.1 mL $^{18}$O-water (enrichment >98%) in a niobium target.
Radio Synthesis Unit:
Equipment: TracerLab Fx-FDG (GE Healthcare, USA).
Configuration: standard plumbing (see IBD_3_2015_I-01) equipped with a silica pre-purification cartridge. Standard cleaning procedure.
HPLC:
Radio-HPLC runs were registered using a Delta 600 pump system (Waters, USA) equipped with a Gabi Star flow-through gamma detector (Raytest, Germany) connected in series to a 996 Photo Diode Array (PDA) UV detector (Waters, USA).
Radio TLC:
Radio-TLC runs were read using a Cyclone PLUS (Perkin-Elmer, USA). Silica gel plates (aluminium) were developed with the eluent mixture and dried before exposure to SR phosphor imager plates.

Chemical and radiochemical purity were controlled by radio HPLC on each formulation before injection. Proper formulations were developed for the administration of the radiolabeled compound of Formula 1b (10% ethanol/saline) and the tracer/tariquidar mix (10% DMSO in 10% glucosate), the second being more critical.

[$^{18}$F] fluoroethylation of compound of formula 1a was conducted in a microfluidic chemistry platform (Advion Nanotek) following a two step reaction. In the first step, an ethylditosylate precursor was labeled in acetonitrile by using the $^{18}$F-fluoride/Kryptofix adduct to yield $^{18}$F-fluoroethyl-tosylate. In the second step, this labeling intermediate was reacted with the compound of formula 1a to afford labeled compound of formula 1b.

The radiochemical procedure was transferred from the microfluidic platform on to a classic vessel radiosynthesis module (GE TracerLab Fx-FDC). The compound of formula 1b was obtained with 4% not decay corrected yield (12% decay corrected) and a radiochemical purity≥95%.

Example 12

Evaluation of compound of Formula 1a in MDCK-Cell for Determining the Activity and Selectivity Towards P-gp and other "Sister Proteins" Namely BCRP, MRP1

A. Three different cell lines have been employed: MDCK-P-gp (fluorescent probe Calcein-AM), MDCK-BCRP (florescent probe Rhodamine) and MDCK-MRP1 (fluorescent probe Calcein-AM). These cells overexpress stably human P-gp or BCRP or MRP1.

i. $EC_{50}$ values of compound of Formula 1a
P-gp $EC_{50}$=8,0±0.2 nM
BCRP $EC_{50}$>500 nM
MRP1 $EC_{50}$>500 nM ii. Comparative EC50 Values of Tariquidar
P-gp $EC_{50}$=4,0±0.2 nM
BCRP $EC_{50}$>80 nM
MRP1 $EC_{50}$>500 nM The above results show that compound of Formula 1a is a potent P-gp ligand whereas it is inactive towards BCRP and MRP1.

The maximal effective concentration ($EC_{50}$) assay for the compound of Formula 1a shows that the compound is active at 8 nM concentration which is 3 times more active and potent than Tariquidar which requires 24 nM concentration as reported in Kazunori Kawamura, et al. $EC_{50}$ assay is a pharmacological potency test which refers to the concentration of a drug, antibody or toxicant which induces a response halfway between the baseline and maximum after a specified exposure time. It is commonly used as a measure of drug's potency.

In order to establish the intrinsic mechanism of compound of Formula 1a in Caco-2 cells has been defined if it was able to deplete ATP. Compound able to deplete ATP can be considered P-gp substrate while ligand unable to deplete ATP is considered P-gp inhibitor.

The MDCK-MDR1 cells were seeded into 96-well microplate in 100 µL of complete medium at a density 2×104 cells/well. The plate was incubated overnight in a humidified atmosphere 5% CO2 at 37° C. The medium was removed and 100 µL of complete medium in the presence or absence of different concentrations of compound of Formula 1a was added. The plate was incubated for 2 h in a humidified atmosphere 5% CO2 at 37° C. Fifty microlitres of mammalian cell lysis solution was added to all wells and the plate was shaken for 5 min in an orbital shaker. Fifty microlitres of substrate solution was added to all wells and the plate was shaken for 5 min in an orbital shaker. The plate was dark adapted for 10 min and the luminescence was measured.

Results of Compound of Formula 1a
ATP-ase cell depletion: at 1 µM 20%
Comparative Tariquidar Results
ATP-ase cell depletion: at 1 µM 30%
The results show that compound of Formula 1a is a somewhat weaker substrate than Pgp substrate.

B. Apparent Permeability in caco-2 cells permits to corroborate the P-gp intrinsic activity of compound. Ligands displaying BA/AB >2 are transported while ligands having BA/AB <2 are not transported by P-gp.

Caco-2 cells were seeded onto a Millicell assay system (Millipore), where a cell monolayer is set in between a filter cell and a receiver plate, at a density of 10,000 cells/well. The culture medium was replaced every 48 h and the cells kept for 21 days in culture. The Trans Epithelial Electrical Resistance (TEER) of the monolayers was measured daily, before and after the experiment, using an epithelial voltohometer (Millicell-ERS). Generally, TEER values greater than 1000× for a 21 day culture, are considered optimal. Caco-2 cells were seeded onto a Millicell assay system (Millipore), where a cell monolayer is set in between a filter cell and a receiver plate, at a density of 10,000 cells/well. The culture medium was replaced every 48 h and the cells kept for 21 days in culture. The Trans Epithelial Electrical Resistance (TEER) of the monolayers was measured daily, before and after the experiment, using an epithelial voltohometer (Millicell-ERS). Generally, TEER values greater than 1000× for a 21 day culture, are considered. After 21 days of Caco-2 cell growth, the medium was removed from filter wells and from the receiver plate, which were filled with fresh MSS buffer (Invitrogen). This procedure was repeated twice, and the plates were incubated at 37° C. for 30 min. After incubation time, the HBSS buffer was removed and drug solutions were added to the filter well at various concentrations (1-100 µM), while fresh MSS was added to the receiver plate. The plates were incubated at 37° C. for 120 min. Afterwards, samples were removed from the apical (filter well) and basolateral (receiver plate) side of the monolayer to measure the permeability. The apparent permeability (Papp), in units of nm/s, was calculated.

Apparent Permeability (B→A/A→B) of compound of Formula 1a was 16±0.7. In comparison, Permeability (B→A/A→B) of Tariquidar is >30.

The results showed that the Apparent permeability is consistent to a P-gp substrate activity. In conclusion, taking into account these assays, the compound of Formula 1a is a Potent P-gp substrate.

Example 13

HPLC Analysis of Compound of Formula 1a

Column: C-18 Kinetex-Phenomenex
Mobile phase: CH3CN/10 mMNaH2PO4=70/30 pH 3.5
Flow: 0.5 mL/min The HPCL chromatogram of compound of Formula 1a is shown in FIG. 1.

Example 14

Protein Plasma Binding (PPB) Assay of Compound of Formula 1a

TABLE 1

| $k_D$ | fb | | $r^2$ | TQI[1] |
|---|---|---|---|---|
| 7.17E-04 | 46.1% | ±3.95% | 0.9380 | 9.2 |

Figure 2:
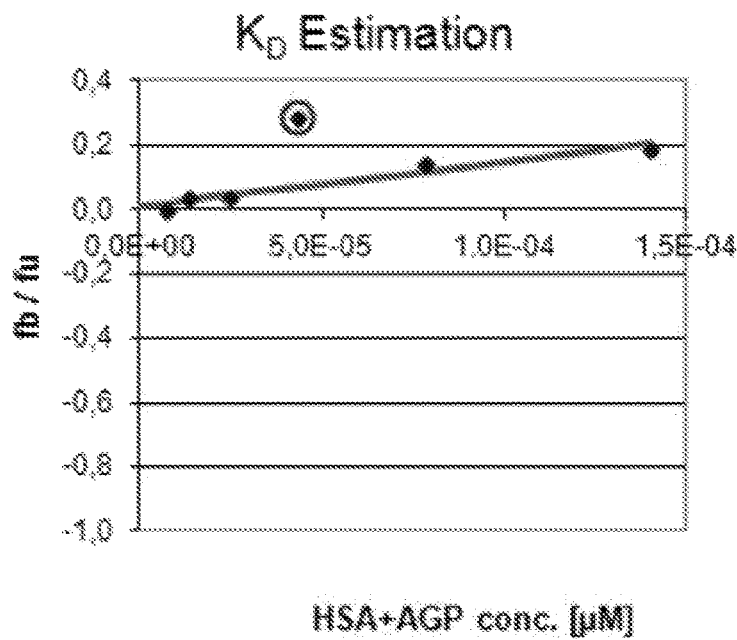
FIG. 2 shows Dissociation constant (kD) estimation, wherein kD=[free Compound of Formula 1a] [free Protein]/[Compound of Formula 1a bound to the protein]

Plasma protein binding is measured in terms of the dissociation constant KD: KD=[compound 1a] [P]/[compound 1a-P], wherein [compound 1a-P] is the concentration of compound of Formula 1a bound to the protein P and where [compound 1a] denotes the free concentration of compound of Formula 1a and [P] denotes the free concentration of protein. The compound of Formula 1a showed a low degree of plasma protein binding (46.1%±3.95%) with a kD=7.17 e-4 M as depicted in FIG. 2. This means there is high free unbound radiotracer available to bind with the target protein for detection.

fb represents an estimation of the fraction bound to plasma proteins based on human serum albumin and human $\alpha_1$ acid glycoprotein. Binding to other low abundance plasma proteins like lipoproteins, transcortin, and sex hormone binding protein is not considered.

The TRANSIL Quality Index (TQI) is based on five independent measures derived from the data analysis. For each individual measure a partial quality score on a scale between 0 and 10 is attributed to the estimate. 0 represents lowest quality, while 10 represents highest quality. The final quality index is a weighted average of the partial quality scores.

The Correlation coefficient $r^2$ from fitting the experimental data to equation also contributes as a partial quality score (Table 2 below). This score has a weight of 3 in the TQI.

TABLE 2

Partial quality scores for the least square model fit of the experimental data to equation

| $r^2$ | Score |
|---|---|
| 0.9999 | 10 |
| 0.999 | 9 |
| 0.99 | 8 |
| 0.9 | 7 |
| 0.8 | 6 |
| 0.7 | 5 |
| 0.6 | 4 |
| 0.5 | 3 |

Example 15

Comparative HPLC Analysis of Tariquidar

Figure 3:
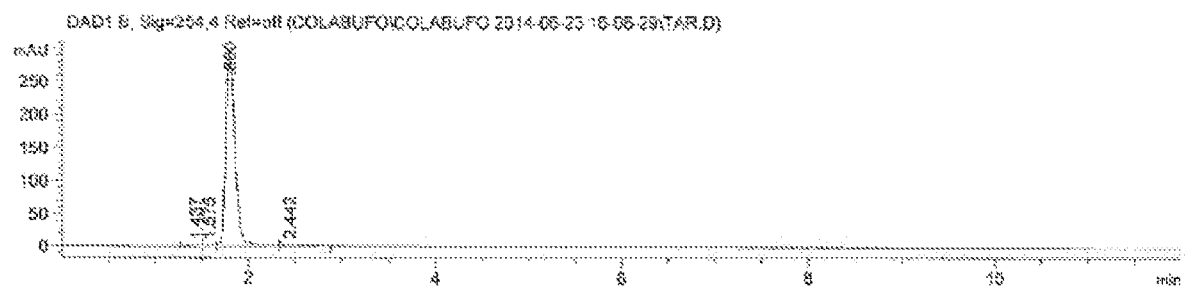
FIG. 3 illustrates Brain uptake (1200-3000 s) of radiolabeled Compound of Formula 1b from microPET dynamic data in P-gp knock-out mice (MDR 1a/b −/−). MicroPET (upper row) and microCT (lower row) images.

Column: C-18 Kinetex-Phenomenex
Mobile phase: CH3CN/10 mMNaH2PO4=70/30 pH 3.5
Flow: 0.5 mL/min
The HPCL chromatogram of Tariquidar is shown in FIG. 3.

Example 16

Comparative Protein Plasma Binding (PPB) Assay of Tariquidar

Figure 4:
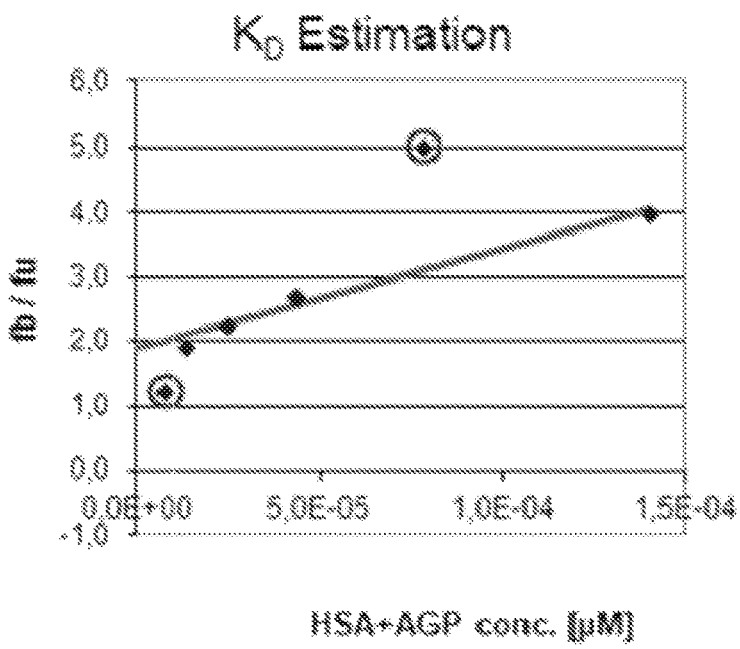
FIG. 4 shows Dissociation constant (KD) estimation wherein KD=[free Tariquidar] [free Protein]/[Tariquidar bound to the protein]

Plasma protein binding is measured in terms of the dissociation constant KD:

$$KD=[TQD] [P]/[TQD-P]$$

where [TQD-P] is the concentration of drug Tariquidar bound to the protein P and where [TQD] denotes the free concentration of Tariquidar and [P] denotes the free concentration of protein. Tariquidar showed a higher degree of plasma protein binding (90.5%±1.06%) with a kD=6.47× 10-5 M as depicted in FIG. 4.

fb represents an estimation of the fraction bound to plasma proteins based on human serum albumin and human $\alpha_1$ acid glycoprotein. Binding to other low abundance plasma proteins like lipoproteins, transcortin, and sex hormone binding protein is not considered.

The TRANSIL Quality Index (TQI) is based five independent measures derived from the data analysis. For each individual measure a partial quality score on a scale between 0 and 10 is attributed to the estimate. 0 represents lowest quality, while 10 represents highest quality. The final quality index is a weighted average of the partial quality scores.

The Correlation coefficient $r^2$ from fitting the experimental data to equation also contributes as a partial quality score (Table 3 below). This score has a weight of 3 in the TQI.

TABLE 3

| $k_D$ | fb | | $r^2$ | TQI[1] |
|---|---|---|---|---|
| 6.47E−05 | 90.5% | ±1.06 | 0.9760 | 7.2 |

The results above showed that the compound of Formula 1a displayed KD=7.17×10-4 while Tariquidar (TQD) displayed KD=6.47×10-5.

The compound of Formula 1a showed higher KD than TQD because the compound of Formula 1a poorly binds plasma proteins whereas TQD binds strongly these proteins. This parameter is important both in terms of Bioavailability and washout for in vivo PET studies.

Example 17

Metabolic Stability of Compound of Formula 1a by Rat Liver Microsomes

Metabolic stability of compound of Formula 1a was evaluated by incubating test compounds with rat liver microsomes and monitoring parent disappearance within 30 mins using HPLC.

| Compound | % remaining at 30 min | Matrix |
|---|---|---|
| Formula 1a | 88 | Rat liver microsomes |

Figure 5:
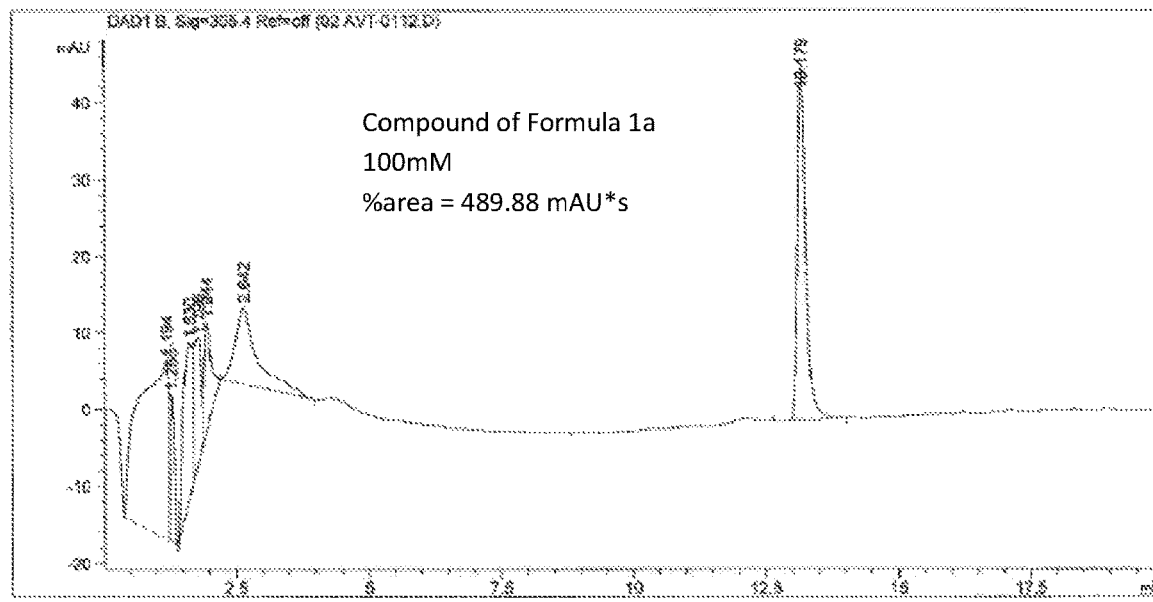
FIG. 5 illustrates Chromatogram of compound of Formula 1a incubated with microsomes fraction only without NADPH regenerating system wherein 489.88 mAU*s represents ligand concentration after incubation $C_{control}$.
Figure 6:
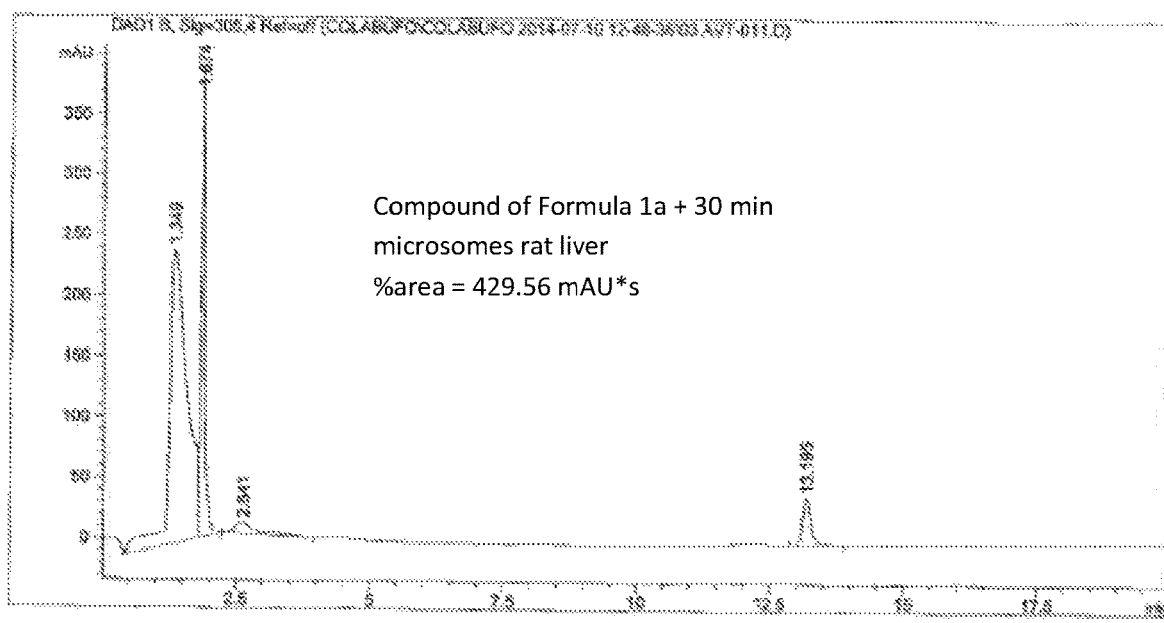
FIG. 6 illustrates Chromatogram of compound of Formula 1a incubated in the presence of microsomes and NADPH regenerating system wherein 429.56 mAU*s represents ligand concentration $C_{parent}$.

Column: KINE IEX-C18
Column temperature: 40° C.
Mobile phase: Gradient. A was 0.1% formic acid in water. B was MeCN. A:B 95:5 to 30:70 over 10 min, to 20:80 over 5 min.
Flow rate: 0.5 ml/min
Injection volume: 50 μL FIG. 5 illustrated a Chromatogram of Formula 1a incubated with microsomes fraction only without NADPH regenerating system wherein 489.88 mAU*s represents ligand concentration after incubation $C_{control}$. FIG. 6 illustrates a Chromatogram of compound of Formula 1a incubated in the presence of microsomes and NADPH regenerating system wherein 429.56 mAU*s represents ligand concentration $C_{parent}$.

Thus, the results above show that the compound of Formula 1a displayed a good metabolic stability since at 30 mins it remains unchanged for 88%.

Metabolites (Human Microsomes)
Unchanged form (%)
After 30 min: 91%
After 60 min 85%

The compound of Formula 1a displayed a good metabolic stability since at 30 mins it remains unchanged for 91% and after 60 min was unchanged for 85%.

Example 18

Cytotoxicity of Compound of Formula 1a

Determination of cell growth was performed using the MTT assay at 24 and 48 h. On day 1, 30,000 cells/well were seeded into 96-well plates in a volume of 100 μL. On day 2, the various drugs concentration (0.1-100 μM) were added. In all the experiments, the various drug-solvents (ethanol, DMSO) were added in each control to evaluate a possible solvent cytotoxicity. After the established incubation time with compound of Formula 1a, MTT(0.5 mg/mL) was added to each well, and after 3 h incubation at 37° C., the supernatant was removed. The formazan crystals were solubilized using 100 μL of DMSO and the absorbance values at 570 and 630 nm were determined on the microplate reader Victor 3 from PerkinElmer Life Sciences.

Results:
At 100 microM, 24 h, 5% at 48 h 15% in MDCK-MDR1
Comparative Results of Tariquidar
At 100 microM, 24 h, 8% at 48 h 19% in MDCK-MDR1

The compound of Formula 1a has been inserted in serosal compartment of everted gas sac and for 120 mins has been tested:
1. The concentration in mucosal compartment
2. The stability in serosal/mucosal compartment The results displayed that the compound of Formula 1a was unable to cross into the mucosal compartment which is expected and typical for P-gp substrate. Moreover the stability at 120 min in serosal compartment is the same that the stability reported with rat microsomes: 83% after 60 min; 75% after 120 min.

The results above show that the compound of Formula 1a is a potent P-gp substrate, with good stability and bound to plasma protein.

In everted gut sac, the compound of Formula 1a seems to be unable to cross BBB and so it is an interesting candidate as PET radiotracer for imaging P-gp in peripheral tumors.

Example 19

Figure 7:
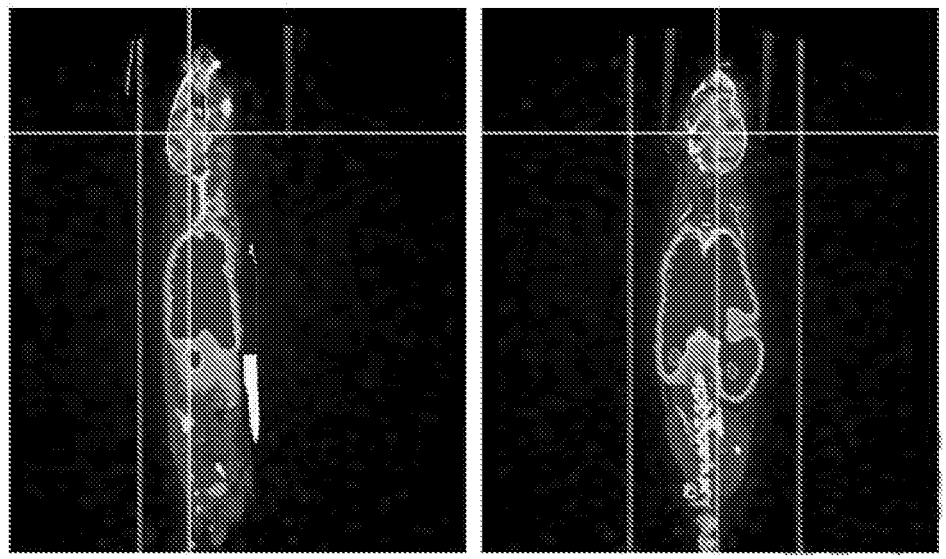
FIG. 7 illustrates brain uptake (1200-3000 s) of compound of Formula 1b from microPET dynamic data following administration of compound of Formula 1b in wild type mice.

Evaluation of In Vivo Bio-Distribution of Compound of Formula 1b using In Vivo MicroPET/CT Studies A set of wild type mice subjects were injected with compound of formula 1b (i.e. [$^{18}$F]-labeled compound of formula 1a). Immediately after injection of the tracer compound, scanning was performed on the subject using a microPET/CT system. The study was conducted in deep anaesthesia (oxygen/1.5-2 isoflurane w/o drug-induction) and the animals were treated by adhering to regulatory, ethical and Animal Welfare guidelines subsequent to obtaining approvals. As shown in FIG. 7, the wild type subjects shown a binding of radiolabeled compound of formula 1b at brain level. The extraction remained constant for the duration of the study and was indicative of a possible selective binding to brain structures. As shown in FIG. 1, the MicroPET and microCT images have been fused for better brain visualization.

Figure 8:
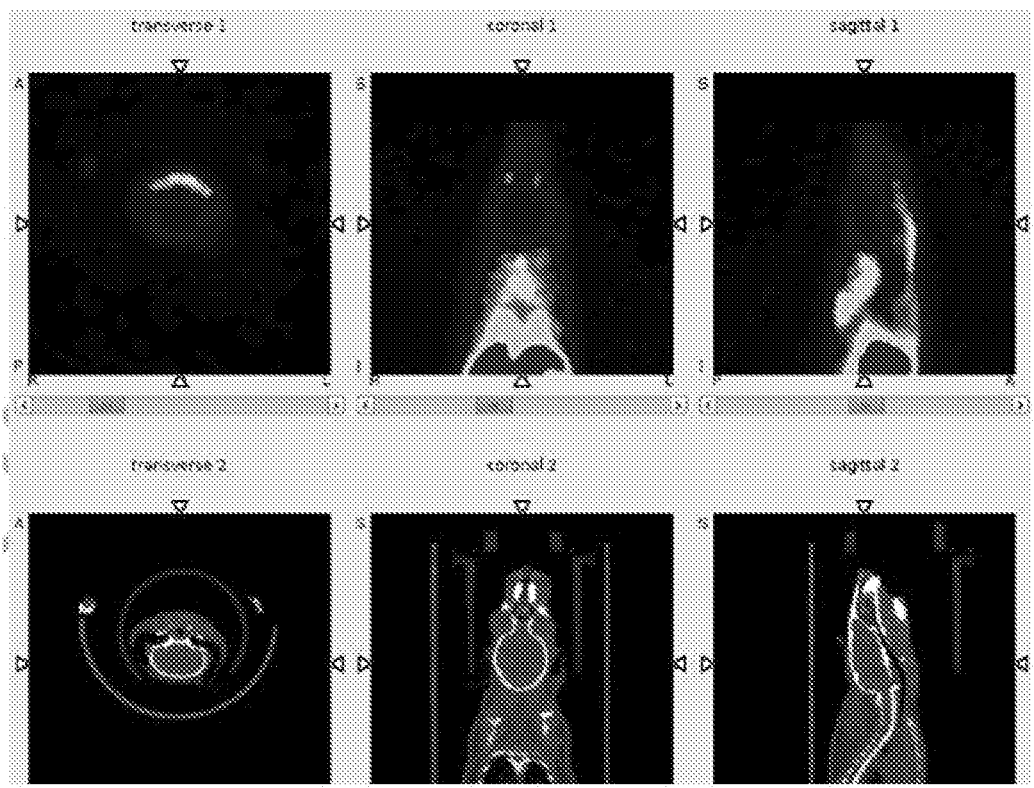
FIG. 8 illustrates brain uptake (1200-3000 s) of compound of Formula 1b from microPET dynamic data following administration (co-injection) of tariquidar and compound of Formula 1b in a wild type mouse.

FIG. 8 illustrates brain uptake (1200-3000 s) of compound of Formula 1b from microPET dynamic data following administration (co-injection) of tariquidar and compound of Formula 1b in a wild type mouse. As shown in FIG. 8, the in vivo uptake at brain level was strongly reduced in the same wild type subjects when the radiotracer (i.e. compound of formula 1b) is administered in the presence of a challenging compound, such as tariquidar, which has the ability to selectively inhibit the P-gp action. In FIG. 8, the upper panel represents MicroPET and the lower panel represents microCT images resulted in the study.

Figure 9:
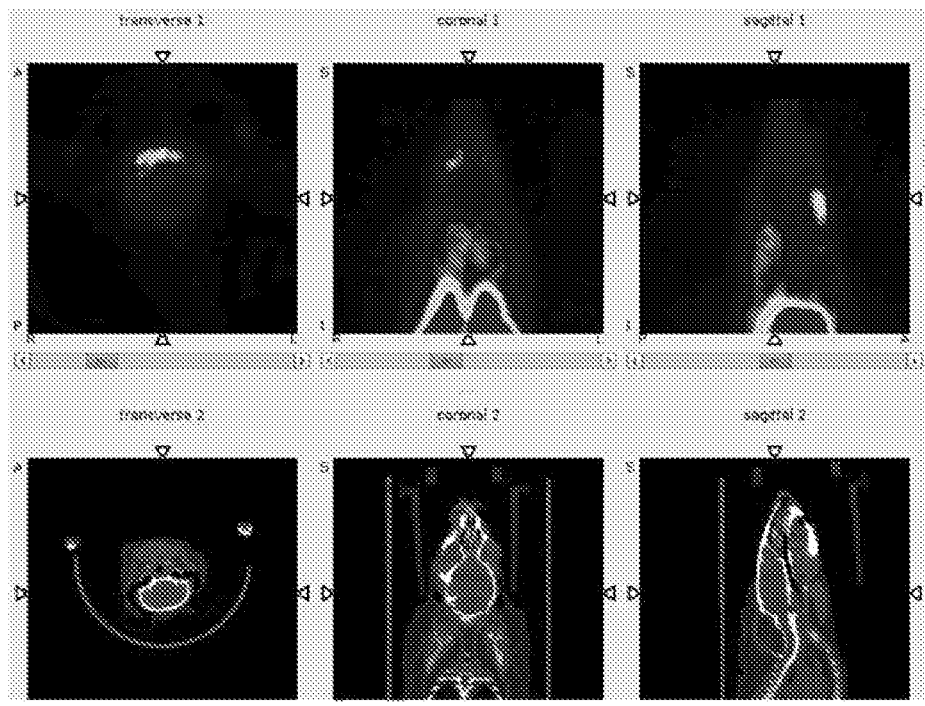
FIG. 9 illustrates brain uptake (1200-3000 s) of compound of Formula 1b from microPET dynamic data following administration (co-injection) of tariquidar and compound of Formula 1b in P-gp knock-out mice (MDR 1a/b −/−).

FIG. 9 illustrates brain uptake (1200-3000 s) of compound of Formula 1b from microPET dynamic data following administration (co-injection) of tariquidar and compound of Formula 1b in P-gp knock-out mice (MDR 1a/b –/–). As shown in FIG. 3, same reduction of uptake at brain level was observed in the subjects void of P-gp sites (i.e. genetically modified knock-out mice: MDR 1a/b –/–).

Figure 10:
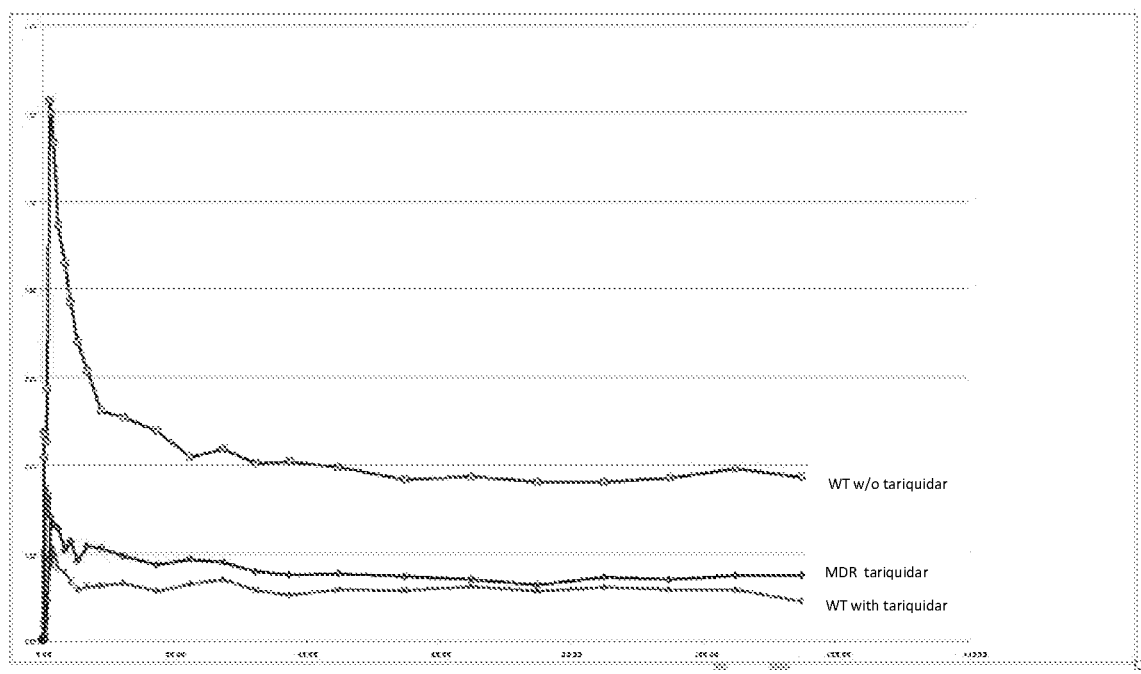
FIG. 10 illustrates brain pharmacokinetics of compound of Formula 1b from microPET dynamic data following administration of compound of Formula 1b in wildtype (red line); wild type co-injection of compound of Formula 1b and 3.7 g/kg of tariquidar (green line); compound of Formula 1b in MDR 1a/b −/− knock-out subjects (blue line).

FIG. 10 illustrates brain pharmacokinetics of compound of Formula 1b from microPET dynamic data following administration of compound of Formula 1b in wildtype (red line); wild type co-injection of compound of Formula 1b and 3.7 g/kg of tariquidar (green line); compound of Formula 1b in MDR 1a/b –/– knock-out subjects (blue line).

ADVANTAGES OF THE INVENTION

The present invention provides a novel compound of Formula 1 capable of being used as a substrate for at least one ABC transporter selected from Pgp, MRP1 or BCRP.

The present invention further provides a novel compound of Formula 1 capable of being used as a radiotracer for PET imaging and targeted radionuclide therapy of one or more conditions that may be regulated or normalized via inhibition of ABC transporter such as Pgp, BCRP and MRP1.

The present invention provides a novel compound of Formula 1 as "first-in-class" PET imaging agent specifically targeted to detect MDR1/Pgp in solid tumours, various types of cancers, disease of the central nervous system, Parkinson, etc.

The present invention provides a novel compound of Formula 1 which can be used as radiotracer for target detection and quantitative imaging of P-glycoprotein and provide a non-invasive means/tool to detect MDR pathology and assign MDR 1/Pgp as the cause of drug resistance in patients exhibiting disease progression or impairment due to failure of chemotherapy.

The present invention provides a novel compound of Formula 1 which can be used as radiotracers for target detection and quantitative imaging of P-glycoprotein and provide a non-invasive means/tool to detect MDR pathology and assign MDR 1/Pgpas the cause of drug resistance in cancer patients exhibiting disease progression or impairment due to failure of chemotherapy to enable for patients stratification based on therapeutic response and guidance to design a bio-marker specific treatment regime and ensure unnecessary toxicities and improve survival outcomes and overall quality of life for the patient.

The present invention concerning the use of a radiolabeled compound of Formula 1 for imaging P-gp function in vitro and in vivo provides an aid in the diagnosis of MDR disorders such as in cancers e.g. brain cancer, breast cancer, bone cancer, etc. and other solid tumours and neurological disorders of the central nervous system such as Parkinson disease, Alzheimer disease, etc.

We claim:
1. A compound of Formula 1a

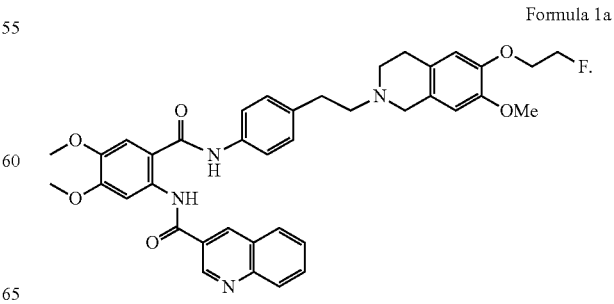

Formula 1a

2. A compound of Formula 1b

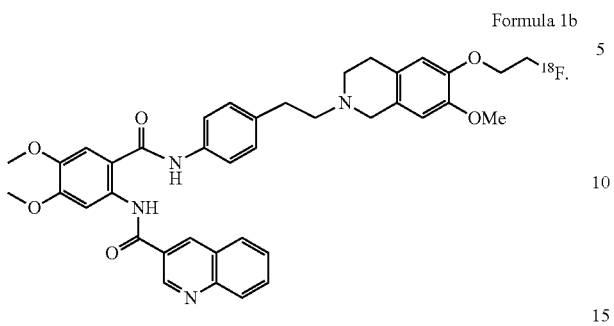

Formula 1b

3. A method for detecting multi drug resistance protein 1 (MDR 1)/P-glycoprotein (P-gp) mediated resistance, the method comprising introducing into a mammal harbouring a tumour or malignant growth a detectable quantity of a radiolabeled compound of Formula 1b according to claim 2 or a pharmaceutically acceptable salt thereof, and detecting multi drug resistance protein 1 (MDR 1)/P-glycoprotein (P-gp) mediated resistance.

4. A method for detecting or imaging a site of targeted localized tissue, the method comprising introducing into a mammal a detectable quantity of a radiolabeled compound of Formula 1b according to claim 2 or a pharmaceutically acceptable salt thereof, and detecting or imaging a site of targeted localized tissue.

5. The method of claim 4, wherein the targeted localized tissue is a tumour or cell growth/proliferation.

* * * * *